US011969438B1

(12) United States Patent
Vashist et al.

(10) Patent No.: US 11,969,438 B1
(45) Date of Patent: *Apr. 30, 2024

(54) POLYOLS AND POLYOL-BASED HYDROGELS WITH ANTI-CANCER ACTIVITY

(71) Applicants: Arti Vashist, Miami, FL (US); Andrea D. Raymond, Miramar, FL (US); Prem Chapagain, Miami, FL (US); Madhavan P. Nair, Coral Gables, FL (US); Carolyn D. Runowicz, Miami, FL (US)

(72) Inventors: Arti Vashist, Miami, FL (US); Andrea D. Raymond, Miramar, FL (US); Prem Chapagain, Miami, FL (US); Madhavan P. Nair, Coral Gables, FL (US); Carolyn D. Runowicz, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/219,443

(22) Filed: Jul. 7, 2023

(51) Int. Cl.
| | | |
|---|---|---|
| *A61K 31/765* | (2006.01) | |
| *A61B 5/00* | (2006.01) | |
| *A61K 9/107* | (2006.01) | |
| *A61K 36/55* | (2006.01) | |
| *A61K 47/36* | (2006.01) | |
| *A61K 47/38* | (2006.01) | |
| *A61K 49/00* | (2006.01) | |
| *A61P 35/00* | (2006.01) | |

(52) U.S. Cl.
CPC .......... *A61K 31/765* (2013.01); *A61B 5/0071* (2013.01); *A61K 9/1075* (2013.01); *A61K 36/55* (2013.01); *A61K 47/36* (2013.01); *A61K 47/38* (2013.01); *A61K 49/0078* (2013.01); *A61P 35/00* (2018.01)

(58) Field of Classification Search
CPC .... A61K 31/765; A61K 9/1075; A61K 36/55; A61K 47/36; A61K 47/38; A61K 49/0078; A61P 35/00; A61B 5/0071
See application file for complete search history.

(56) References Cited

U.S. PATENT DOCUMENTS

| | | | |
|---|---|---|---|
| 10,344,100 | B1 | 7/2019 | Vashist et al. |
| 2014/0286872 | A1 | 9/2014 | Zhang et al. |
| 2020/0383932 | A1 | 12/2020 | Nair et al. |
| 2022/0313617 | A1* | 10/2022 | Nair .................... A61K 9/5146 |

OTHER PUBLICATIONS

Alli, Sema et al. "Castor oil-based graft copolymers: synthesis, characterization antimicrobial activity and antiproliferative effects against breast cancer cell lines." Polymer Bulletin 79:11177-11199, Jan. 14, 2022.
Ding, Hong et al. "Enhanced blood-brain barrier transmigration using a novel Transferrin-embedded fluorescent magnetoliposome nanoformulation." Nanotechnology 25(5):1-30, Feb. 7, 2014.
Eberhardt, Jerome et al. "AutoDock Vina 1.2.0: New Docking Methods, Expanded Force Field, and Python Bindings." J. Chem. Inf. Model. 61(8):3891-3898, Jul. 19, 2021.
Engelberth, Sarah A. et al. "Development of Nanoscale Approaches for Ovarian Cancer Therapeutics and Diagnostics." Critical Reviews in Oncogenesis 19(3-4):281-315, (Year: 2014).
Haber, Tom et al. "Specific targeting of ovarian tumor-associated macrophages by large, anionic nanoparticles." Proceedings of the National Academy Of Sciences 117(33):19737-19745, (Year: 2020).
Jain, Rakesh K. "Normalizing Tumor Microenvironment to Treat Cancer: Bench to Bedside to Biomarkers." Journal of Clinical Oncology 31(17):2205-2219, Jun. 10, 2013.
Jayson, Gordon C. et al. "Ovarian cancer." Lancet 384(9951):1376-1388, Oct. 11, 2014.
Junise, V. "Development And Characterization of Inhaled Chitosan Nanoparticles Loaded with Isoniazid." Journal of Pharmaceutical Technology, Research and Management 2(2):159-170, Nov. 2014.
Khanmohammadi, Mohammadreza et al. "Investigation of Size and Morphology of Chitosan Nanoparticles used in Drug Delivery System Employing Chemometric Technique." Iranian Journal of Pharmaceutical Research 14(3):665-675, (Year: 2015).
Lin, Yuxin et al. "Tumor-associated macrophages in tumor metastasis: biological roles and clinical therapeutics applications." Journal of Hematology & Oncology 12(76):1-16, (Year: 2019).
Martinelli, Marcia et al. "Hybrid films based on hydroxylated castor oil and titanium (IV) isopropoxide." J. Sol-Gel Sci. Technol. 52:202-209, Jul. 25, 2009.
Matulonis, Ursula A. et al. "Ovarian cancer." Nature reviews Disease primers 2(1):1-22, (Year: 2016).
Mensah, M. B. et al. "Castor oil: a suitable green source of capping agent for nanoparticle syntheses and facile surface functionalization." Royal Society Open Science 5(8):1-19, (Year: 2019).
Miao, Shida et al. "Vegetable-oil-based polymers as future polymeric biomaterials." Acta Biomaterialia 10(4):1692-1704, (Year: 2014).
Morris, Garrett M. et al. "AutoDock4 and AutoDockTools4: Automated Docking with Selective Receptor Flexibility." Journal of computational chemistry 30(16):2785-2791, Dec. 2009.
Nagel, Gregor et al. "Matrix Metalloproteinase-sensitive Multistage Nanogels Promote Drug Transport in 3D Tumor Model." Theranostics 10(1):91-108, (Year: 2020).

(Continued)

*Primary Examiner* — Genevieve S Alley
*Assistant Examiner* — Long Bao Dang
(74) *Attorney, Agent, or Firm* — SALIWANCHIK, LLOYD & EISENSCHENK

(57) ABSTRACT

The present invention provides compositions and methods for selectively treating a cancer or tumor utilizing an effective amount of a vegetable oil-derived polyol or hydrogel particles comprising a vegetable oil-derived polyol. In some embodiments, the cancer is a gynecologic cancer, specifically an ovarian cancer. In other aspects, the present invention provides a method of targeting and imaging various tumors and/or tumor associated macrophages (TAMs).

15 Claims, 10 Drawing Sheets

(56) References Cited

OTHER PUBLICATIONS

Pettersen, Eric F. et al. "UCSF Chimera—A Visualization System for Exploratory Research and Analysis." Journal of computational chemistry 25(13):1605-1612, (Year: 2004).
Ravi, Rangnath et al. "Fabrication of Superparamagnetic Bimetallic Magnesium Nanoferrite Using Green Polyol: Characterization and Anticancer Analysis in Vitro on Lung Cancer Cell Line A549." ACS Applied Bio Materials 5(11):5365-5376, (Year: 2022).
Sagar, Vidya et al. "Chapter 15: Nanogels for Biomedical Applications: Challenges and Prospects." The Royal Society of Chemistry, pp. 290-300, (Year: 2017).
Schmitz, William R. & Wallace, John G. "Epoxidation of Methyl Oleate With Hydrogen Peroxide." The Journal of the American Oil Chemists' Society 31(9):363-365, (Year: 1954).
Shadyro, Oleg et al. "In Vivo Antitumoral Effects of Linseed Oil and its Combination With Doxorubicin." Frontiers in Pharmacology vol. 13, Article 882197, pp. 1-14, Jun. 2022.
Sharmin, Eram et al. "Epoxidation, hydroxylation, acrylation and urethanation of Linum usitatissimum seed oil and its derivatives." European Journal of Lipid Science and Technology 109(2):134-146, Feb. 13, 2007.
Sharmin, Eram et al. "Studies on microwave synthesized polyol linseed oil." Materials Research Laboratory, Department of Chemistry, pp. 43-45 (Year: 2010).
Sharmin, Eram et al. "Synthesis, characterization, antibacterial and corrosion protective properties of epoxies, epoxy-polyols and epoxy-polyurethane coatings from linseed and Pongamia glabra seed oils." International Journal of Biological Macromolecules 40:407-422, (Year: 2007).
Sierra-Martin, B. & Fernandez-Barbero, A. "Multifunctional hybrid nanogels for theranostic applications." Soft Matter 11(42):8205-8216, (Year: 2015).
Soni, Kruti S. et al. "Nanogels: an overview of properties, biomedical applications and obstacles to clinical translation." J. Control Release 240:109-126, Oct. 28, 2016.
Sumer, Baran & Gao, Jinming et al. "Theranostic nanomedicine for cancer." Nanomedicine 3(2):137-140, (Year: 2008).
Sung, Yoon Nak et al. "The Anti-Cancer Effect of Linusorb B3 from Flaxseed Oil through the Promotion of Apoptosis, Inhibition of Actin Polymerization, and Suppression of Src Activity in Glioblastoma Cells." Molecules 25(24):1-17, Dec. 12, 2020.
Tajau, Rida et al. "Surface functionalisation of poly-APO-b-polyol ester cross-linked copolymers as core-shell nanoparticles for targeted breast cancer therapy." Scientific reports 10(1):1-17, (Year: 2020).
Trott, Oleg & Olson, Arthur J. "AutoDock Vina: improving the speed and accuracy of docking with a new scoring function, efficient optimization and multithreading." J. Comput. Chem. 31(2):455-461, Jan. 30, 2010.
Vashist, Arti et al. "Development of Multifunctional Biopolymeric Auto-Fluorescent Micro-and Nanogels as a Platform for Biomedical Applications." Frontiers in Bioengineering and Biotechnology 8(315):1-16, Apr. 2020.
Vrignaud, Sandy et al. "Reverse micelle-loaded lipid nanocarriers: A novel drug delivery system for the sustained release of doxorubicin hydrochloride." European Journal of Pharmaceutics and Biopharmaceutics 79:197-204, (Year: 2011).

\* cited by examiner

POLYOLS AND POLYOL-BASED HYDROGELS WITH ANTI-CANCER ACTIVITY

BACKGROUND

Cancer is one of the major health concerns resulting in highest morbidity and mortality world-wide. Gynecologic cancers include cancers that begin in a woman's reproductive organs. In the United States alone, it is estimated that approximately 100,000 women are diagnosed with gynecologic cancers each year. Gynecologic cancers include carcinomas of the uterine cervix (cervical cancer), uterus, ovary, as well as malignancies of the fallopian tube, vagina, vulva, and choriocarcinomas. Ovarian cancer is the deadliest of all gynecologic cancers and the fifth leading cause of cancer-related deaths in women. Ovarian cancer is complex, as it is not a single disease, but is further divided into at least five different histological subtypes, including high-grade serous, low-grade serous, mucinous, clear cell, and endometrioid ovarian cancer. The high-grade serous ovarian cancer accounts for approximately 75% of ovarian cancers, and recent studies suggest that the majority of this subtype may originate in the fallopian tube.

The subtypes of ovarian cancer are distinct diseases based on diverse identifiable factors which include cells of origin, molecular compositions, clinical features, and different treatment responses. Survival statistics of ovarian cancer have not improved significantly over the last three decades, largely due to late-stage diagnosis, poor prognosis, and the high recurrence rate associated with development of chemoresistance, as surviving cancer cells can evolve in response to administered therapy. Thus, improvements in early cancer detection and/or therapeutic methods are highly desirable.

Standard treatment for newly diagnosed ovarian cancer involves cytoreductive surgery and platinum-based chemotherapy. Chemotherapy, anti-angiogenic agents, poly(ADP-ribose) inhibitors, or immunotherapies are the major treatment modalities used in the treatment of ovarian cancer. However, the current chemotherapeutic treatments result in major side effects due to lack of specific targeting and dosages. Selectivity of most anti-cancer compounds known to date is poor; thus, resulting in adverse effects on healthy cells. Nanotechnology-based strategies have been garnering attention as a way to address these problems and improve therapeutic/diagnostic methods. Examples of nanotechnology-based strategies include formulations utilizing functionalized nanoparticles incorporating diagnostic, imaging, or drug-delivery properties, such as Abraxane® (a formulation wherein paclitaxel is bound to albumin nanoparticles as an alternative delivery agent) and other formulations such as the PEGylated liposomal nano-encapsulation of doxorubicin (doxil) reported by Vrignaud, S., et al., *Reverse Micelle-loaded Lipid Nanocarriers: a Novel Drug Delivery System for the Sustained Release of Doxorubicin Hydrochloride*, Eur. J. Pharm. and Biopharm., 79(1), 197-204 (2011).

The traditional trend in nanomedicines is to modulate the bio-distribution and target site-accumulation of systemically administered drugs resulting in improved efficacy and reduced toxicity. Importantly, nanomedicines should typically be combined with pharmacological and physical co-treatments, being integrated in multimodal combination therapy regimens.

Among various types of nanoparticles, hydrogels are microparticles or nanoparticles developed using hydrophilic biopolymers. They are also called nanogels (NG) if they are nanoparticles. Nanogels can be composed of naturally occurring polymers, synthetic polymers, or a combination thereof. The properties and characteristics of nanogels—such as encapsulation efficiency, tissue compatibility, and biodegradability—are influenced by their chemical compositions. They can be attractive candidates for designing formulations to effectively deliver chemotherapeutic or diagnostic agents to target sites. However, existing nanogels require significant improvement for specific cell or organ targeting, as no more than 5-10% of the injected dose is estimated actually to reach the target site.

In the case of nanogels designed to carry therapeutic agents and target tumors, the likelihood of nanogels reaching the core of the tumors is low. Targeted delivery of nanogels can be passive or active. Passive targeting takes advantage of the general tendency of nanoparticles to leak into solid tumors or inflamed tissues through their defective leaky and loosely compacted vasculature and impaired lymphatic drainage. This process is known as the enhanced permeability and retention (EPR) effect. However, contrary to the widely held belief that the EPR effect improves targeted delivery, more is needed to amass nanoparticles in sufficient concentrations at the target site. Active targeting, on the other hand, is achieved by the conjugation of nanogels to receptor-specific ligands. However, a significant challenge of active targeting lies in finding receptors that are exclusively expressed on the tissue of interest.

Additionally, many intravenously administered nanogels end up reaching organs such as the liver and spleen, where nanogels are rapidly cleared by the resident phagocytic cells such as monocytes and macrophages.

The final efficacy of a nanogel-based delivery system is governed by a complex interplay of parameters like their size, shape, charge, composition, surface properties, and the cargo they carry.

Previously, auto-fluorescent, biopolymer-based hydrogel nanoparticles and microparticles prepared from chitosan and hydroxyethyl cellulose with a crosslinking agent and a linseed oil-derived polyol have been reported. See e.g., U.S. Pat. No. 10,344,100, WO2020/247730. The linseed oil-derived polyol used in these particles is a chemically modified forms of linseed oil, more specifically, a hydroxylated form of linseed oil. These references are silent regarding the anti-cancer effect of vegetable oil-derived polyols themselves, in particular linseed oil-derived polyol, or hydrogel nanoparticles and microparticles comprising a vegetable oil derived polyol.

BRIEF SUMMARY

The present invention provides compositions and methods for selectively treating cancer or tumor utilizing an effective amount of a vegetable oil-derived polyol or hydrogel nanoparticles and/or microparticles comprising a vegetable oil-derived polyol. In some embodiments, the cancer or tumor is a gynecologic cancer, specifically an ovarian cancer. Advantageously, a vegetable oil-derived polyol and hydrogel nanoparticles and/or microparticles comprising a vegetable oil-derived polyol are biodegradable.

In some embodiments, modification of hydrogels using a vegetable-oil derived polyol adds on to their surface functionalization. It imparts advantageous properties such as high stability of the hydrogels and specificity to target cancerous or tumorous cells. In specific embodiments, the vegetable oil-derived polyol comprises a linseed oil-derived polyol.

The present invention provides a composition and a method of effectively and selectively targeting cancerous or tumorous cells without decreasing the viability of healthy cells. The present invention also provides a safe and cost-effective cancer or tumor treatment, as vegetable oil-derived polyols and hydrogel particles according to the present invention can be produced safely and with low cost on an industrial scale.

In other aspects, the present invention provides a method of targeting and imaging various tumors or tumor associated macrophages (TAMs).

DETAILED DESCRIPTION

Figure 1:
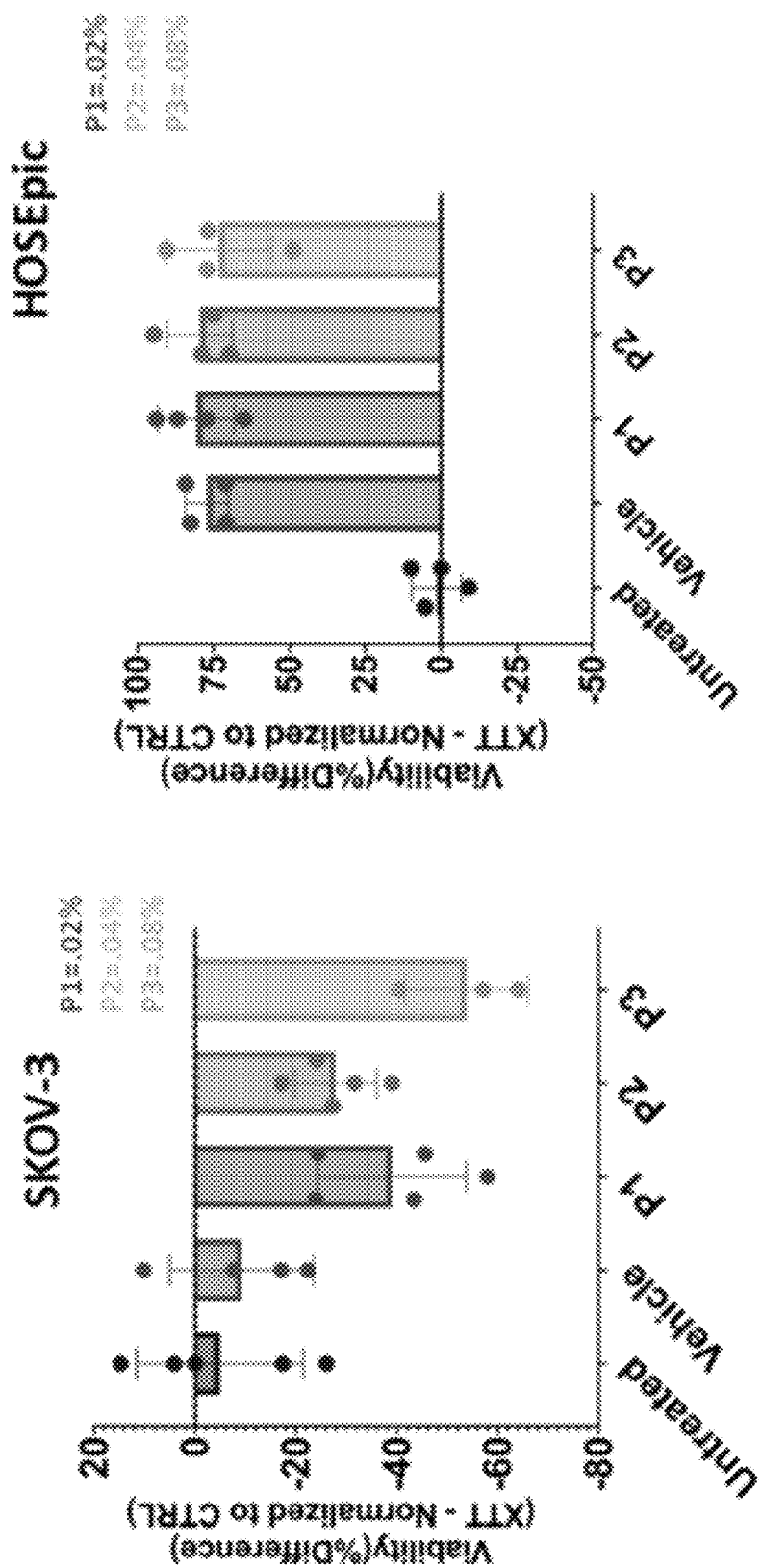
FIG. 1 provides graphs showing the results of the XTT cell viability assay of healthy human ovarian epithelial cells (HOSEpic) and human ovarian cancer cells (SKOV3) after exposure to increasing concentrations (0.02%, 0.04%, 0.08%) of linseed oil-derived polyol.

The present invention provides compositions and methods for the treatment of cancer or tumor utilizing a vegetable oil-derived polyol or hydrogel nanoparticles and/or microparticles comprising a vegetable oil-derived polyol. In specific embodiments, the vegetable oil-derived polyol comprises a linseed oil-derived polyol. Advantageously, a vegetable oil-derived polyol and hydrogel nanoparticles and/or microparticles comprising a vegetable oil-derived polyol are biodegradable.

In some embodiments, the hydrogel nanoparticles and/or microparticles are formed from biopolymers, such as chitosan, hydroxyethyl cellulose (HEC), and hydroxylpropylcellulose (HPC), and further from a vegetable oil-derived polyol such as linseed oil-derived polyol.

In some embodiments, the cancer or tumor is a gynecologic cancer. In more specific embodiments, the cancer is an ovarian cancer, a cervical cancer, or a fallopian tube cancer. In a particular embodiment, the cancer is an ovarian cancer.

Vegetable Oil-Derived Polyol

The vegetable oil-derived polyols according to the present invention are derived from vegetable oils. A "vegetable oil" as used herein is a natural, plant-based oil including, but are not limited to, castor oil, soybean oil, camelina oil, palm kernel oil, palm oil, jatropha oil, rapeseed oil, sunflower oil, linseed oil, olive oil, black seed oil, and almond oil. Major components of vegetable oils are triglycerides. Fatty acid compositions of the vegetable oil, including the degree of unsaturation, vary depending on the vegetable oil source. Preferably, the vegetable oil-derived polyol according to the present invention is derived from linseed oil. In some embodiments, a vegetable oil does not comprise castor oil.

Polyols derived from vegetable oils as used herein are chemically modified vegetable oils, the chemical modification involving hydroxylation of the fatty acid chains of triglycerides, diglycerides, or monoglycerides of vegetable oils. In more specific embodiments, the hydroxylation is dihydroxylation of olefins in the fatty acid chains of triglycerides, diglycerides, or monoglycerides of vegetable oils. Triglycerides, diglycerides, and monoglycerides of vegetable oils generally have long fatty acid hydrocarbon chains, typically of about C12 to about C20. The vegetable-oil derived polyols range in the degrees of unsaturation, e.g., C—C double bond, and they typically have a lesser degree of unsaturation compared to their unmodified counterparts. Non-limiting examples of fatty acids in vegetable oils that can be chemically modified include oleic acid, linoleic acid, γ-linoleic acid, α-linolenic acid, and/or arachidonic acid. Preferably, the vegetable oils according to the invention comprise triglycerides of one or more of such fatty acids.

Various methods known in the art may be used to obtain polyols from vegetable oils according to the present invention. Such methods include, but are not limited to, Baeyer oxidation of double bonds of polyunsaturated fatty acids or alcoholysis of a vegetable oil with glycerol. Other strategies include, but are not limited to, ring opening of reactive epoxidized oils with various nucleophilic agents, such as MeOH, phenol, cyclohexanol, diethyl phosphate, phthalic anhydride, diethylene glycol, or lactic acid. Other methods include, but are not limited to, thiol-ene coupling, ozonolysis, hydroformylation, and photochemical oxidation, which are generally described in Miao S. et al., Vegetable-oil-based polymers as future polymeric biomaterials, Acta Biomaterialia 10, 1692-1704, 1693-1694 (2004). In other embodiments, the vegetable-oil derived polyols according to the present invention are synthesized through microwave irradiation in the absence of an organic solvent as disclosed in Sharmin, E. et al., Studies on Microwave Synthesized Polyol Linseed Oil, BVAAP, 18(1), p. 43-45 (2010). In other embodiments, the vegetable-oil derived polyols according to the present invention are obtained via epoxidation and hydroxylation such as the process described in Sharmin, E. et al., *Synthesis, Characterization, Antibacterial and Corrosion Protective Properties of Epoxies, Epoxy-Polyols and*

*Epoxy-Polyurethane Coatings from Linseed and Pongamia Glabra Seed Oils*, International Journal of Biological Macromolecules, 40(5): p. 407-422 (2007) ("Sharmin et al., 2007"), which is incorporated herein by reference in its entirety.

In some embodiments, the vegetable oil-derived polyol used in the present invention has been purified and/or it is substantially free of vegetable oil that was used to obtain the polyol.

Preferably, the vegetable oil used to obtain a vegetable oil-derived polyol according to the present invention is linseed oil, which is also known as flaxseed oil or flax oil. Linseed oil can be obtained from the dried, ripened seeds of the flax plant (*Linum usitatissimum*). Linseed oil is mostly a triglyceride, and is known for its high content of α-linolenic acid. The preferred vegetable oil-derived polyol according to the present invention is linseed oil-derived polyol, which is obtained via dihydroxylation of alkenes in the fatty acid chains of the linseed oil triglycerides. In some embodiments, linseed oil according to the present invention is chemically modified via epoxidation and hydroxylation consistent with the process described in Sharmin et al., 2007. Briefly, the reaction involves mixing of linseed oil and glacial acetic acid with hydrogen peroxide (with a few drops of sulfuric acid), in a three-necked round bottomed flask equipped with a cold water condenser, nitrogen inlet tube, and thermometer. The ratio of double bonds:acetic acid:hydrogen peroxide is kept at 1:0.5:1.5. After mixing, the temperature of the reaction mixture is raised and maintained for the required time periods. In some embodiments, the temperature is raised to 50-55° C. and then to 75±5° C. In some embodiments, the temperature is raised to within the range of 58-70° C. The ethereal solution of the final product is washed with sodium bicarbonate aqueous solution, distilled water, and sodium chloride aqueous solution, and is further dried over anhydrous sodium sulfate. Ether is removed from the final product in a rotary vacuum evaporator at 45±5° C., or 45-58° C., or in some embodiments at room temperature. The final product is golden yellow colored.

In some embodiments, the linseed oil-derived polyol comprises compounds of the chemical structure of Formula (I):

In some embodiments, the linseed oil-derived polyol used in the present invention has been purified and/or it is substantially free of linseed oil that was used to obtain the polyol.

As used herein, the terms "purified" or "isolated," as used herein in connection with reaction products means the products are substantially free of other compounds, such as reagents that were used to make the products. In certain embodiments, purified products are at least 60% by weight of the product(s) of interest. Preferably, the preparation is at least 75%, 80%, or 85%, more preferably at least 90%, 91%, 92%, 93%, 94%, 95%, 96%, 97%, 98%, or 99% (w/w) of the desired product(s) by weight. In some embodiments, purified products are at least 99.5 or 99.9% by weight of the product(s) of interest. Purity is measured by any appropriate standard method, for example, by column chromatography, thin layer chromatography, or high-performance liquid chromatography (HPLC) analysis.

The present invention utilizes a vegetable oil-derived polyol to treat cancer or tumor. In some embodiments, the vegetable oil-derived polyols are administered alone or as a component of hydrogel particles according to the present invention. In some embodiments, the vegetable oil-derived polyols are administered as a component of other compounds, or nano- or micro-particles other than the hydrogel particles as described herein. For example, a vegetable oil-derived polyol maybe used to modify non-hydrogel nanocarriers. As further non-limiting examples, the vegetable oil-derived polyol can be used to modify various polymers such as polyurethanes, Poly(vinyl alcohol) (PVA), Polyvinyl chloride (PVC), Polyvinylpyrrolidone (PVP). Other polymers include but are not limited to biopolymers, guar gum, poly(lactic-co-glycolic acid) (PLGA), chitin, polylactic acid (PLA), Hyaluronic acid, Polyacrylamide, as well as synthetic polymers. The vegetable oil-derived polyol can also be used to modify various coatings and resins, waterborne polymers, nanocomposite materials which include dendrimers, liposomes, etc. Furthermore, the vegetable oil-derived polyol can be used to modify nanocapsules, magnetic particles as well as the carbon nanotubes for functionalization. In some embodiments, the vegetable oil-derived polyol enhances selectivity towards cancerous cells and imparts anti-cancer properties to the modified compounds or nano- or micro-particles. In certain embodiments,

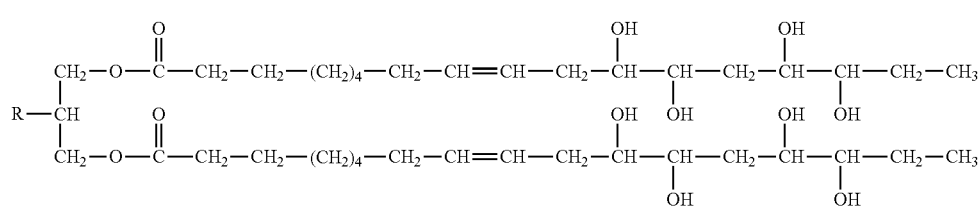

R being:

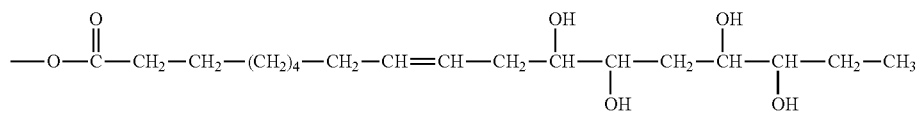

the vegetable oil-derived polyol as a component of hydrogel particles, other compounds or particles comprises a linseed oil-derived polyol.

In other embodiments, the vegetable oil-derived polyol is administered without forming a part of any compounds, particles, or carriers, including hydrogel nanoparticles and/or microparticles. In certain embodiments, the vegetable oil-derived polyol administered alone comprises a linseed oil-derived polyol.

In some embodiments, the vegetable oil-derived polyol according to the invention is a linseed oil-derived polyol. In some embodiments, the vegetable oil-derived polyol according to the invention is a linseed oil-derived polyol, and contains no other vegetable oil-derived polyol that materially affects the anti-cancer effects of the linseed oil-derived polyol.

Surprisingly, it has been discovered that polyols derived from vegetable oils such as the linseed oil-derived polyol have anti-cancer or anti-tumor effects. A vegetable oil-derived polyol according to the present invention selectively targets cancerous cells or tumorous cells over healthy cells to impart anti-cancer or anti-tumor effects. Without being bound by a particular theory, vegetable oil-derived polyol such as linseed oil-derived polyol reduces the viability of cancerous cells or tumorous cells by selectively inducing apoptosis of those cells or interfering with their proliferation. In some embodiments, linseed oil-derived polyol selectively and negatively affects the viability of human ovarian cancer cells (SKOV3) by inducing their apoptosis while promoting proliferation in healthy cell lines (HOSEpic). Furthermore, molecular docking studies demonstrated that linseed oil-derived polyol interacts with leptin, leptin receptor, and the insulin-like growth factor type 1 receptor (IGF-1R), suggesting the polyol's role in the mitigation or prevention of cancer development and progression. (See FIGS. 8, 9A, and 9B).

Advantageously, the vegetable oil-derived polyols according to the present invention, such as linseed oil-derived polyol, are biodegradable and biocompatible with healthy cells.

Hydrogel Microparticles and Nanoparticles (Hydrogel Particles)

In some embodiments, a vegetable oil-derived polyol according to the present invention is a component of biopolymer-based hydrogel microparticles and nanoparticles that are used to treat cancer or tumor. Thus, in one aspect, hydrogel particles according to the present invention are nanoparticles or microparticles that comprise a gel of a biopolymer and a vegetable oil-derived polyol. In some embodiments, a crosslinking agent known in the art, including, but is not limited to, glutaraldehyde, is incorporated to make hydrogel particles according to the present invention.

In some embodiments, the vegetable oil-derived polyol comprises a linseed oil-derived polyol. In some embodiments, the vegetable oil-derived polyol according to the invention is a linseed oil-derived polyol. In some embodiments, the vegetable oil-derived polyol according to the invention is a linseed oil-derived polyol, and contains no other vegetable oil-derived polyol that materially affects the anti-cancer effects of the linseed oil-derived polyol.

In some embodiments, the hydrogel nanoparticles or microparticles according to the present invention are cross-linked gels having a spherical shape. In specific embodiments, the hydrogel nanoparticles or microparticles according to the present invention are from about 20 nm to about 1000 μm in cross-section. In further embodiments, the hydrogel nanoparticles or microparticles according to the present invention are from about 40 nm to about 500 μm in cross-section.

In some embodiments, hydrophobically modifying hydrogels using a vegetable-oil derived polyol adds on to their surface functionalization of the hydrogels and imparts advantageous properties such as high stability and specificity to target cancerous or tumorous cells. The inventors of the present invention have serendipitously discovered that at high doses of hydrogels comprising a vegetable-oil derived polyol, in particular linseed oil-derived polyol, human ovarian cancer cells (SKOV3) and human cervical cancer cells (HeLa) are sensitive to hydrogel-induced toxicity. In some embodiments, hydrogels according to the present invention induce apoptosis of cancerous cells (SKOV3) significantly more than of healthy cells (HOMEC).

In preferred embodiments, hydrogel nanoparticles or microparticles according to the present invention are prepared by a water-in-oil emulsion polymerization method, such as the methods described in U.S. Pat. No. 10,344,100, incorporated herein by reference. In an exemplary embodiment, a water-in-oil emulsion is prepared comprising at least one biopolymer, an oil component, water, and an emulsifying agent, the water being suspended in a continuous phase of the oil component. A crosslinking agent and at least one vegetable oil-derived polyol are added to the water-in-oil emulsion, whereupon stirring the water-in-oil emulsion forms the hydrogel nanoparticles/microparticles comprising the vegetable oil-derived polyol. Thus, in some embodiments, hydrogel nanoparticles or microparticles according to the present invention are prepared based on the following general steps:

1. Preparing a water-in-oil emulsion by adding an aqueous phase comprising at least one biopolymer dropwise to a mixture of an oil component and an emulsifying agent, the aqueous phase being suspended in a continuous phase of the oil component;
2. adding a crosslinking agent to the water-in-oil emulsion;
3. adding the at least one vegetable oil-derived polyol to the water-in-oil emulsion; and
4. stirring the water-in-oil emulsion to form hydrogel nanoparticles or microparticles comprising the vegetable oil-derived polyol.

An oil component used in the preparation of hydrogel nanoparticles or microparticles according to the present invention may be any oil suitable to serve as a continuous oil phase in an water-in-oil emulsion, such as a paraffin oil. The paraffin oil can be heavy liquid paraffin oil. An emulsifying agent may be, but is not limited to, Tween 80. A crosslinking agent may be, but is not limited to, glutaraldehyde. In specific embodiments, glutaraldehyde is not in the form of Glutaraldehyde-Saturated Toluene (GST).

Biopolymers are polymers produced from natural sources, either chemically synthesized from a biological material or biosynthesized by living organisms. Preferably, biopolymers according to the present invention are water miscible. Non-limiting examples of biopolymers that can be used to prepare hydrogel nanoparticles and microparticles according to the present invention include chitosan, hydroxyethyl cellulose (HEC), hydroxylpropylcellulose (HPC), carboxymethyl cellulose (CMC), methyl cellulose (MC), starches, and pectin. The biopolymers according to the present invention are preferably chitosan and hydroxyethyl cellulose (HEC). In specific embodiments, chitosan and HEC have a weight ratio of, for example, 1:1, 2:1, 3:1, 4:1, 1:2, 1:3, 2:3, 3:2, 4:3, 3:4, 5:2, 5:3, 5:4, 2:5, 3:5, 4:5, 6:5, 5:6, 7:2, 7:3, 7:4, 7:5, 7:6, 6:7, 5:7, 4:7, 3:7, or 2:7.

Chitosan is a bioactive, biocompatible, biodegradable, and nontoxic hydrocolloid, with hemostatic, bacteriostatic, and other properties favorable for a range of industrial and biomedical applications. Chitosan is a polysaccharide comprising 1-4-linked residues of 2-amino-2-deoxy-β-D-glucose (glucosamine) and 2-acetamido-2-deoxy-β-D-glucose (N-acetylglucosamine). In some embodiments, chitosan can play a significant role in the formation of the crosslinked hydrogel particles.

In a preferred embodiment, the biopolymer chitosan used to form hydrogel nanoparticles and/or microparticles has a medium molecular weight of 190-310 kDa, 190-300 kDa, 200-300 kDa, 200-290 kDa, 200-280 kDa, 200-270 kDa, 200-260 kDa, 200-250 kDa, 200-220 kDa, 190-200 kDa, or 250-300 kDa.

In specific embodiments, the biopolymer chitosan, when measured for a 1 wt. % solution of the chitosan in 1% acetic acid at 25° C., has a viscosity from about 200 cP to about 800 cP, from about 200 cP to about 700 cP, from about 300 cP to about 700 cP, from about 300 cP to about 600 cP, from about 400 cP to about 600 cP, from about 400 cP to about 500 cP, from about 200 cP to about 300 cP, from about 300 cP to about 400 cP, from about 500 cP to about 600 cP, from about 600 cP to about 700 cP, or from about 700 cP to about 800 cP.

In some embodiments, copolymers of sodium alginate and acrylamide may also be combined with one or more biopolymers to form the hydrogel nanoparticles and/or microparticles. In specific embodiments, hydrogel nanoparticles and/or microparticles according to the present invention are not formed from polymers other than biopolymers. In more specific embodiments, hydrogel nanoparticles and/or microparticles according to the present invention are not formed from polymers other than chitosan and hydroxyethyl cellulose (HEC).

In some embodiments, the hydrogel nanoparticles and/or microparticles according to the present invention may further include a magnetic component, for example, magnetic nanoparticles (MNP) and other metal oxide particles. MNPs are a class of nanoparticle that can be manipulated using a magnetic field, and comprise a magnetic material such as iron, nickel, or cobalt. A typical example of MNP is iron oxide (III) nanoparticles. In some embodiments, MNPs such as $Fe_2O_3$ are prepared using a co-precipitation method as disclosed in Ding et al., *Enhanced Blood-brain Barrier Transmigration Using a Novel Transferrin-Embedded Fluorescent Magnetoliposome Nanoformulation*, Nanotechnology, (25) 055101 (2014).

In some embodiments, an MNP is encapsulated by a gel comprising a biopolymer, a vegetable oil-derived polyol, and optionally a cross-linking agent to obtain the hydrogel nanoparticles and/or microparticles according to the present invention. In further embodiments, hydrogel nanoparticles and/or microparticles according to the present invention are formed by encapsulating iron oxide (III) nanoparticles as an MNP with a cross-linked gel comprising chitosan, HEC, linseed oil-derived polyol, and glutaraldehyde. By way of non-limiting example, magnetic hydrogel nanoparticles and/or microparticles according to the present invention are prepared by using water-in-oil emulsion polymerization techniques to encapsulate an MNP, which involve adding an MNP (e.g., $Fe_2O_3$) to a polymer solution of chitosan and hydroxyethyl cellulose in 1% (v/v) acetic acid and blending the mixture for about 30 mins. The mixture is then added dropwise to a separate mixture of liquid paraffin oil and 1% (w/w) Tween 80, with a stirring rate of 14000 rpm on a magnetic stirrer. The mixing of the solution is continued for 20 minutes followed by the addition of glutaraldehyde (5 ml) for another 10 minutes. Thereafter, linseed oil-derived polyol is added to the reaction mixture under continued stirring at 14000 rpm for 5 hours. The particles are washed thoroughly with n-hexane to remove excess oil, and excess glutaraldehyde is deactivated by 0.1 M glycine. The washed hydrogel particles are dried at room temperature to obtain the hydrogel nanoparticles and/or microparticles comprising an MNP as a magnetic component.

In some embodiments, hydrogel nanoparticles and/or microparticles comprising a magnetic component such as iron oxide (III) exploit their magnetic character to target the cancerous sites in a patient. In specific embodiments, the magnetic hydrogel particles according to the present invention target sites of gynecologic cancer, more specifically ovarian cancer, fallopian tube cancer, and/or cervical cancer. Preferably, the hydrogel particles comprising a magnetic component according to the present invention targets sites of ovarian cancer.

In certain embodiments, hydrogel nanoparticles and/or microparticles comprising a magnetic component such as iron oxide (III) have improved selectivity over hydrogel nanoparticles and/or microparticles having no magnetic component in targeting the cancerous sites in a patient. In further embodiments, the magnetic hydrogel particles according to the present invention has a higher selectivity than hydrogel nanoparticles and/or microparticles having no magnetic component in reducing ovarian cancer cell viability. In some embodiments, the magnetic hydrogel particles according to the present invention have a higher selectivity than hydrogel nanoparticles and/or microparticles having no magnetic component in inducing apoptosis and/or programmed cell death of ovarian cancer cells.

In other embodiments, the hydrogel particles according to the present invention do not include a magnetic component. In further embodiments, the hydrogel particles according to the present invention do not include a metal or metal oxide component. In some embodiments, the hydrogel particles according to the present invention exhibit selectivity and impart anti-cancer or anti-tumor effects without a magnetic component.

In some embodiments, the hydrogel nanoparticles and/or microparticles according to the present invention may further include inorganic particles such as those comprising gold or silver. In other embodiments, the hydrogel nanoparticles and/or microparticles according to the present invention do not include inorganic particles such as gold or silver. In some embodiments, the hydrogel particles according to the present invention impart anti-cancer or anti-tumor effects without inorganic particles.

In specific embodiments, the hydrogel nanoparticles and/or microparticles may be loaded with one or more cargo, including but is not limited to, therapeutic agents and/or imaging agents such as fluorophores. The therapeutic agent may be for treating cancer or tumor and may be small molecule drugs, proteins, peptides, and/or nucleic acids. In some embodiments, the therapeutic agent for treating cancer or tumor is intended to treat a gynecologic cancer. In more specific embodiments, the therapeutic agent for treating cancer or tumor is intended to treat an ovarian cancer, cervical cancer, or fallopian tube cancer. In other embodiments, the hydrogel nanoparticles and/or microparticles are not loaded or otherwise chemically associated with any additional therapeutic agent and/or imaging agent. In some embodiments, the hydrogel nanoparticles and/or microparticles according to the present invention are not loaded with any cargo.

In some embodiments, the hydrogel nanoparticles and/or microparticles have controlled sizes, e.g., from micro to nano. Various techniques and methods can be used to control the size of the hydrogel nanoparticles and/or microparticles according to the present invention, including, but are not limited to, sonication, probe sonication, filtration through membrane filters having pore sizes such as 0.1 µm, 0.2 µm, 0.4 µm, or 0.8 µm. Additionally or alternatively, the rate of stirring and duration of stirring can influence the size of the hydrogel particles.

The hydrogel particles can be designed in various sizes. In specific embodiments, the hydrogel nanoparticles or microparticles according to the present invention are from about 20 nm to about 1000 µm. In further embodiments, the hydrogel nanoparticles or microparticles according to the present invention are from about 40 nm to about 500 µm. In some embodiments, the hydrogel particles range in size, for example, from about 50 nm to 300 µm, from about 50 nm to 250 µm, from about 50 nm to 200 µm, from about 50 nm to 150 µm, from about 50 nm to 100 µm, from about 50 nm to 50 µm, from about 50 nm to 25 from about 50 nm to 10 µm, from about 50 nm to 5 µm, from about 50 nm to 1 µm, from about 50 nm to 900 nm, from about 50 nm to 800 nm, from about 50 nm to 700 nm, from about 50 nm to 600 nm, from about 50 nm to 500 nm, from about 50 nm to 400 nm, from about 50 nm to 300 nm, from about 50 nm to 200 nm, from about 50 nm to 100 nm, from about 100 nm to 300 µm, from about 150 nm to 300 in, from about 200 nm to 300 µm, from about 500 nm to 300 µm, from about 1 µm to 300 µm, from about 5 µm to 300 µm, from about 10 µm to 250 µm, from about 20 µm to 200 µm, or from about 50 µm to 100 µm.

In some embodiments, the hydrogel particles according to the present invention exhibit auto-fluorescence, which can be used for cellular imaging. In specific embodiments, hydrogel nanoparticles/microparticles comprising a gel of chitosan, HEC, linseed oil-derived polyol, and glutaraldehyde exhibit auto-fluorescence over a concentration range of 10-100 µg/ml in host cells including human ovarian cancer cells (SKOV3). This auto-fluorescence allows the hydrogel particles according to the present invention to be utilized as an in vivo imaging-based diagnostic tool as part of cancer treatment.

The hydrogel particles according to the present invention display a dynamic wide range of emission wavelengths, 450 to 750 nm and 710 to 810 nm, which permits simultaneous in vivo imaging. Their high stability in aqueous solution at physiological pH, 7.4, allows good shelf-life in solution and in a dry form at room temperature, for at least 6 months, while retaining their auto-fluorescence property.

In some embodiments, hydrogel nanoparticles and microparticles according to the present invention are advantageously biocompatible with healthy cells.

In some embodiments, the present invention provides hydrogel nanoparticles and microparticles comprising a gel of chitosan, hydroxyethyl cellulose (HEC), and linseed oil-derived polyol that have anti-cancer and/or anti-tumor properties. Optionally, glutaraldehyde as a crosslinking agent is an additional component to form the gel. Advantageously, the hydrogel particles according to the present invention have selective anti-cancer effects on cancer cells in the absence of additional anti-cancer agents. In some embodiments, the hydrogel particles comprising linseed oil-derived polyols according to the present invention have anti-cancer or anti-tumor effects.

In further embodiments, the hydrogel particles according to the present invention selectively and significantly reduce ovarian cancer cell viability in the absence of additional anti-cancer agents. In some embodiments, the hydrogel particles according to the present invention selectively induce apoptosis and/or programmed cell death of ovarian cancer cells in the absence of additional anti-cancer agents.

In some embodiments, the present invention provides hydrogel nanoparticles and microparticles comprising a gel of chitosan, HEC, and linseed oil-derived polyol that are both auto-fluorescent and anti-cancerous/anti-tumorous without loading or otherwise including any additional therapeutic or imaging agent. Optionally, glutaraldehyde as a crosslinking agent is an additional component to form the gel. In other embodiments, the hydrogel nanoparticles and microparticles comprising a gel of chitosan, HEC, and linseed oil-derived polyol according to the present invention serve as an effective delivery vehicle for a therapeutic or imaging agent, selectively targeting cancerous or tumorous cells. Optionally, glutaraldehyde as a crosslinking agent is an additional component to form the gel. Cancers that are targeted by the hydrogel particles of the present invention include gynecologic cancer, more specifically ovarian cancer, fallopian tube cancer, and/or cervical cancer.

In some embodiments, the present invention provides magnetic hydrogel nanoparticles and microparticles that are also auto-fluorescent and anti-cancerous/anti-tumorous without loading or otherwise including any additional therapeutic or imaging agent. In further embodiments, such magnetic hydrogel nanoparticles and microparticles comprise an MNP that is encapsulated by a gel comprising chitosan, HEC, and linseed oil-derived polyol. Optionally, glutaraldehyde as a crosslinking agent is an additional component to form the gel.

In some embodiments, the autofluorescence and inclusion of components for magnetic behavior allows magnetic hydrogel nanoparticles and microparticles of the present invention to possess target specificity (in some embodiments improved specificity) combined with in vivo imaging. These magnetic hydrogel particles may be further tagged, either chemically or physically, with antigen/antibody for enhanced specificity for a cancer of interest. In some embodiments, magnetic hydrogel particles of the present invention can be loaded with one or more cargo, including but not limited to, therapeutic agents and/or imaging agents such as fluorophores.

Advantageously, hydrogel nanoparticles and microparticles comprising a gel of chitosan, HEC, and linseed oil-derived polyol according to the present invention are capable of being suspended in various solvents such as water, PBS, and 0.1% CMC solution. Optionally, glutaraldehyde as a crosslinking agent is an additional component to form the gel. The hydrogel nanoparticles and microparticles have a broad concentration range that is biocompatible. In some embodiments, the concentration range is about 1 µg/ml to about 100 µg/ml.

In further embodiments, hydrogel nanoparticles and microparticles according to the present invention are highly biodegradable. In further embodiments, the hydrogel nanoparticles and microparticles according to the present invention comprise a gel of chitosan, HEC, linseed oil-derived polyol, and glutaraldehyde. Biodegradability of hydrogel nanoparticles and microparticles according to the present invention is particularly important to treatment of cancers, more specifically gynecologic cancers. Many nano- or microparticles known in the art that are utilized or being considered for cancer treatment have a molecular weight far above the renal threshold and thus cannot be removed from the body through the kidneys. Even if the nano- or microparticles can be degraded into smaller polymer fragments for eventual renal elimination, there is a risk of cellular accumulation of such fragments by sequestration in the lysosomal compartments. Thus, it is critical that the particles utilized in cancer treatment are biodegradable and thus do not accumulate in cells and organs (e.g., liver, kidneys, lungs etc.) so as to avoid undesirable side effects. The biodegradability of hydrogel nanoparticles and microparticles according to the present invention is highly advantageous and relevant to the treatment of gynecologic cancers, as a standard treatment schedule for gynecologic cancers typically requires multiple treatments, e.g., about six cycles of treatment followed by several more cycles of maintenance therapy. This high frequency of treatment cycles creates a greater likelihood of accumulation of nano- or microparticles in the body unless the particles are biodegradable. Hydrogel nanoparticles and microparticles according to the present invention are biodegradable, and thus are suitable to be used in treating gynecologic cancers.

Composition

In some embodiments, vegetable oil-derived polyols such as linseed oil-derived polyol or the hydrogel nanoparticles and/or microparticles according to the invention are formulated into a pharmaceutical composition, optionally comprising a pharmaceutically acceptable carrier or excipient.

In some embodiments, a composition comprises a vegetable oil-derived polyol, preferably a linseed oil-derived polyol, from about 0.001% to about 2.00%, from about 0.001% to about 1.00%, from about 0.001% to about 0.90%, from about 0.001% to about 0.80%, from about 0.001% to about 0.70%, from about 0.001% to about 0.60%, from about 0.001% to about 0.50%, from about 0.001% to about 0.40%, from about 0.001% to about 0.30%, from about 0.001% to about 0.20%, from about 0.001% to about 0.19%, from about 0.001% to about 0.18%, from about 0.001% to about 0.17%, from about 0.001% to about 0.16%, from about 0.001% to about 0.15%, from about 0.001% to about 0.14%, from about 0.001% to about 0.13%, from about 0.001% to about 0.12%, from about 0.001% to about 0.11%, or from about 0.001% to about 0.10% by weight of the total composition. In some embodiments, a composition comprises a vegetable oil-derived polyol, preferably a linseed oil-derived polyol, from about 0.001% to about 0.09%, from about 0.001% to about 0.08%, from about 0.001% to about 0.07%, from about 0.001% to about 0.06%, from about 0.001% to about 0.05%, from about 0.001% to about 0.04%, from about 0.001% to about 0.03%, from about 0.001% to about 0.02%, from about 0.001% to about 0.01% by weight of the total composition.

"Pharmaceutically acceptable carrier" or "pharmaceutically acceptable excipient" is as understood by those skilled in the art, and is useful in preparing a pharmaceutical composition that is generally safe and neither biologically nor otherwise undesirable. A pharmaceutically acceptable carrier or excipient is approved or approvable by a regulatory agency of the Federal or State government, listed in the U.S. Pharmacopoeia, or other generally recognized pharmacopoeia for use in animals and more particularly in humans. Pharmaceutically acceptable carrier or excipient includes any and all solvents, dispersion media, coatings, antibacterial and antifungal agents, isotonic, and absorption delaying agents, and the like. The use of such media and agents for pharmaceutically active substances is well known in the art. Except insofar as any conventional media or agent is incompatible with the active ingredient (i.e., vegetable oil-derived polyol or hydrogel particles according to the present invention) in its anti-cancer and/or anti-tumor effect, its use in the therapeutic compositions of the invention is contemplated.

Examples of carriers or excipients suitable for use in pharmaceutical compositions are known in the art and such embodiments are within the purview of the invention. The pharmaceutically acceptable carriers and excipients, include, but are not limited to, aqueous vehicles, water-miscible vehicles, non-aqueous vehicles, stabilizers, solubility enhancers, isotonic agents, buffering agents, suspending and dispersing agents, wetting or emulsifying agents, surfactants, complexing agents, sequestering or chelating agents, cryoprotectants, lyoprotectants, thickening agents or other viscosity modifiers, pH adjusting agents, fillers, and inert gases. Other suitable excipients or carriers include, but are not limited to, dextran, glucose, maltose, sorbitol, xylitol, fructose, sucrose, and trehalose.

In some embodiments, no natural vegetable oils, such as linseed oil or castor oil, are a component of the pharmaceutical composition.

In some embodiments, a pharmaceutical composition comprises one or more additional therapeutic agent for treating cancer or tumor, aside from a vegetable oil-derived polyol or hydrogel particles according to the present invention. In some embodiments, a therapeutic agent for treating cancer or tumor is loaded to the hydrogel particles of the present invention. In other embodiments, a therapeutic agent for treating cancer or tumor is not loaded to hydrogel particles of the present invention but is included in the same composition as the hydrogel particles. In other embodiments, a therapeutic agent for treating cancer or tumor is loaded to hydrogel particles of the present invention, and the same or a different therapeutic agent for treating cancer or tumor is included in the same composition as the hydrogel particles. In other embodiments, a pharmaceutical composition according to the present invention does not comprise any additional therapeutic agent for treating cancer or tumor, whether it is loaded or not loaded to the hydrogel particles. A therapeutic agent for treating cancer or tumor may be small molecule drugs, proteins, peptides, and/or nucleic acids. Non-limiting examples of therapeutic agent for treating cancer or tumor include doxorubicin, topotecan, lurotecan, paclitaxel, cyclopamine, gossypol, cisplatin, docetaxel, curcumin, gemcitabine, quercetin, C-6 ceramide, topoisomerase I inhibitors, camptothecin, oxaliplatin and its analogues, carboplatin and its analogues, and Platinum (II) complexes.

A vegetable oil-derived polyol or hydrogel particles according to the present invention are, in some embodiments, formulated into suitable pharmaceutical preparations such as aerosols, inhalants, tablets, capsules, or elixirs for oral administration or in sterile solutions or suspensions for parenteral administration. In some embodiments, the hydrogel particles according to the present invention are formulated in oral tablets. In other embodiments, hydrogel particles according to the present invention are formulated into preparations suitable for subcutaneous administration, intraperitoneal injections (IP), or Intravenous (IV) administration. Typically, the vegetable oil-derived polyol or the hydrogel nanoparticles and microparticles described above are formulated into pharmaceutical compositions using techniques and procedures known in the art.

In one embodiment, the composition comprising the vegetable oil-derived polyol or the hydrogel nanoparticles and microparticles according to the invention, together with a conventional carrier or excipient, may thus be placed into the form of solids including pills, troches, tablets, cachets, lozenges, filled capsules, powder and pellet forms, and liquids such as aqueous or non-aqueous solutions, suspensions, emulsions, elixirs, and capsules filled with the same. The composition may further comprise conventional ingredients in conventional proportions.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. Various other materials may be present as coatings or for otherwise modifying the physical form of the solid unit dosage form. For instance, tablets, pills, or capsules may be coated with gelatin, wax, shellac, or sugar, and the like.

In some embodiments, the vegetable oil-derived polyol or the hydrogel particles according to the present invention can be used as an aqueous suspension formulation for introduction to a subject by an injection, for the topical application to an internal or external body surface, or within a liquid filled capsule. The aqueous solution can be employed in a water-in-oil emulsion in which the continuous phase vehicle of the oil can be exploited for surface properties to retain the vegetable oil-derived polyol or the hydrogel particles formulation in a selected environment of the body. The aqueous solution can be employed in an oil-in-water emulsion in which the continuous phase vehicle of the aqueous suspension can be augmented by oil-soluble or oil-suspendable adjuvants.

The pharmaceutical dosage forms suitable for injection or infusion can include sterile aqueous solutions or dispersions or sterile powders comprising the vegetable oil-derived polyol or the hydrogel particles according to the present invention. Preferably, the ultimate dosage form should be sterile, fluid, and stable under the conditions of manufacture and storage. The liquid carrier or vehicle can be a solvent or liquid dispersion medium comprising, for example, water, a polyol (for example glycerol, propylene glycol, liquid polyethylene glycols, and the like), vegetable oils, nontoxic glyceryl esters, and suitable mixtures thereof. In some embodiments, no natural vegetable oils, such as linseed oil or castor oil, are used in the pharmaceutical composition according to the present invention.

Pharmaceutical compositions for topical administration can be formulated as ointments, creams, lotions, gels, or as a transdermal patch comprising the vegetable oil-derived polyol or the hydrogel particles according to the present invention. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for intra-nasal administration are also encompassed by the present invention. Such intra-nasal compositions comprise the vegetable oil-derived polyol or the hydrogel particles according to the present invention, in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol. The vegetable oil-derived polyol or the hydrogel particles may be combined with an inert powdered carrier and inhaled by the subject or insufflated.

Pharmaceutical compositions for administration by inhalation or insufflation and comprising the vegetable oil-derived polyol or the hydrogel particles according to the present invention can be provided in the form of a dry powder composition, and a suitable powder base such as lactose or starch. Such powder composition can be provided in unit dosage form, for example, in capsules, cartridges, gelatin packs, or blister packs, from which the powder can be administered with the aid of an inhalator or insufflator.

In some embodiments, a pharmaceutical composition according to the present invention is adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is administered by injection, an ampoule of sterile water for injection or saline can be provided so that the ingredients may be mixed prior to administration.

In some embodiments, a pharmaceutical composition according to the present invention can be used in treatment regimens that employ one or more other therapeutic agents in a separate composition where the pharmaceutical composition according to the present invention is administered simultaneously or sequentially with the one or more other therapeutic agents to treat a cancer or tumor in a subject.

Methods

In another aspect, the present invention provides a method of treating a cancer or tumor in a subject. In some embodiments, a method according to the present invention comprises administering to a subject in need of treatment of a cancer or tumor an effective amount of a vegetable oil-derived polyol such as linseed oil-derived polyol and optionally a pharmaceutically acceptable carrier or excipient. In further embodiments, a method according to the present invention comprises administering to a subject in need of treatment of a cancer or tumor an effective amount of hydrogel microparticles and/or nanoparticles comprising a vegetable oil-derived polyol such as linseed oil-derived polyol, and optionally a pharmaceutically acceptable carrier or excipient.

In certain embodiments, the vegetable oil-derived polyol according to the invention comprises a linseed oil-derived polyol. In some embodiments, the vegetable oil-derived polyol is linseed oil-derived polyol according to the present invention. In some embodiments, the vegetable oil-derived polyol according to the invention is a linseed oil-derived polyol, and contains no other vegetable oil-derived polyol that materially affects the anti-cancer effects of the linseed oil-derived polyol.

Tumors as used herein are a swelling part of the body, caused by an abnormal growth of tissue, whether benign (non-cancerous), premalignant, or malignant (cancerous). Thus, tumors may overlap with cancers. In some embodiments, tumors being treated according to the present invention are malignant. In some embodiments, tumors being treated according to the present invention are premalignant.

Cancers as used herein may include, but are not limited to, prostate cancer, gallbladder cancer, intrahepatic biliary tract cancer, biliary tract cancer, oral cancer, pharyngeal cancer, laryngeal cancer, tongue cancer, duodenal cancer, eye tumor, mediastinal cancer, sinus cancer, renal pelvic cancer, heart cancer, glioblastoma, neuroblastoma, liver cancer, bone cancer, pancreatic cancer, skin cancer, head and neck cancer, breast cancer, lung cancer, skin or intraocular malignant melanoma, kidney cancer, uterine cancer, ovarian cancer, colon cancer, rectal cancer, anal region cancer, colorectal cancer, stomach cancer, testicular cancer, fallopian tube cancer endometrial carcinoma, cervical carcinoma, vaginal carcinoma, vulvar cancer, non-Hodgkin's lymphoma, esophageal cancer, small intestinal cancer, endocrine system cancer, thyroid cancer, parathyroid cancer, adrenal gland cancer, soft tissue sarcoma, urethral cancer, penile cancer, childhood cancer, lymphocytic lymphoma, bladder cancer, ureter cancer, renal pelvic carcinoma, central nervous system (CNS) cancer, primary CNS lymphoma, tumor angiogenesis, spinal cancer, brainstem glioma, pituitary adenoma, Kaposi's sarcoma, epidermal cancer, squamous cell carcinoma, multiple myeloma, B-cell lymphoma, Hodgkin's lymphoma, acute myeloid lymphoma, chronic myeloid leukemia, chronic lymphocytic leukemia, follicular lymphoma, diffuse large B-cell lymphoma, Burkitt's lymphoma, immune large-cell lymphoma, progenitor B-lymphoblastic lymphoma, mantle cell lymphoma, acute lymphoblastic lymphoma, mycosis fungoides, anaplastic large-cell lymphoma, acute myeloid leukemia, acute lymphoblastic leukemia, hepatoblastoma, retinoblastoma, peritoneal cancer, brain tumor, thymic cancer, T-cell lymphoma or precursor T-lymphoblastic lymphoma, and any combination of the above cancers.

In some embodiments, a cancer or tumor being targeted by the present invention is in a variety of stages including newly diagnosed, relapsed, refractory, progressive disease, remission, and others. In some embodiments, the cancer or tumor being treated is a newly diagnosed cancer. In some embodiments, the cancer or tumor is a recurrent cancer (e.g., a recurrent gynecologic cancer such as recurrent epithelial ovarian cancer, recurrent fallopian tube cancer, recurrent primary peritoneal cancer, or recurrent endometrial cancer). In some embodiments, the present invention is applicable to treatment of metastatic cancers.

In more specific embodiments, a cancer or tumor being treated according to the present invention is a gynecologic cancer. Gynecologic cancers are cancers of the female reproductive tract including cervix, vagina, vulva, uterus, fallopian tube, and ovary. In some embodiments, the gynecologic cancer is associated with homologous recombination repair deficiency, homologous repair deficiency ("HRD"), and/or BRCA1/2 mutation(s). In some embodiments, the gynecologic cancer includes, but is not limited to, uterine, endometrial, ovarian, cervical, vulvar, fallopian tube, or vaginal cancer.

In more specific embodiments, a cancer or tumor being targeted by the present invention is an ovarian cancer. The ovarian cancer being treated may be epithelial and/or non-epithelial in origin, and includes, but is not limited to, High-Grade Serous Carcinoma, Clear Cell Carcinoma, Endometrioid Carcinoma, Low-Grade Serous Carcinoma, and Mucinous Carcinoma, mixed epithelial carcinoma adenocarcinoma not otherwise specified (NOS), malignant Brenner's tumour, transitional cell carcinoma, undifferentiated carcinoma.

In further embodiments, a cancer being targeted by the present invention is a fallopian tube cancer, also known as tubal cancer. In some embodiments, a cancer being targeted by the present invention is a cervical cancer.

"Subject" refers to an animal, such as a mammal, for example a human. The methods described herein can be useful in both human therapeutics and veterinary applications. In some embodiments, the subject is a mammal (including animal models of disease), and in some embodiments, the subject is human. Non-limiting examples of subjects include canine, porcine, rodent, feline, bovine, poultry, equine, human, and a non-human primate.

The term "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, or the symptom of the disease or condition. The term "treating" refers to any indication of success in the treatment or amelioration of a pathology or condition, including any objective parameter such as abatement, remission, lessening of the rate of worsening, lessening severity of the disease, or diminishing of symptoms.

In certain embodiments, the vegetable oil-derived polyol such as linseed oil-derived polyol and/or the hydrogel particles of the present invention may be administered by inhalation, orally, intra-nasally, topically, intramuscularly, subcutaneously, intrathecally, intravenously or intraperitoneally by infusion or injection. In some embodiments, the hydrogel particles according to the present invention are administered orally, subcutaneously, intraperitoneally, or intravenously.

The particular mode of administration and the dosage regimen will be selected by the attending clinician, taking into account the particulars of the case (e.g., the subject, the disease, the disease state involved). Treatment may involve daily or multi-daily doses of compound(s) over a period of a few days to months, or even years.

In some embodiments, a suitable dose of hydrogel particles according to the present invention will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

In some embodiments, hydrogel particles according to the present invention can be conveniently administered in unit dosage form, containing for example, about 0.05 to about 10000 mg, about 0.5 to about 10000 mg, about 5 to about 1000 mg, or about 50 to about 500 mg of the hydrogel nanoparticles and/or microparticles per unit dosage form.

The vegetable oil-derived polyol such as linseed oil-derived polyol and/or the hydrogel particles according to the present invention may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations.

Optionally and as discussed herein, a method according to the present invention utilizes one or more additional therapeutic agents for treating a cancer or tumor to provide a combination therapy. The additional therapeutic agent(s) may be loaded to the hydrogel particles of the present invention or otherwise formulated in the same composition as the hydrogel particles or vegetable oil-derived polyol of the invention. In some embodiments, the additional therapeutic agent(s) are provided in a composition that is separate from the composition comprising the hydrogel particles or vegetable oil-derived polyol of the present invention. Such separate composition is administered simultaneously with or at a time that is some time before or after the administration of the composition comprising the hydrogel particles or vegetable oil-derived polyol of the present invention. In some embodiments, the additional therapeutic agent(s) are included in the compositions of the present invention within a therapeutically useful and effective concentration range, as determined by methods that are known in the medical and pharmaceutical arts. The concentration of any particular additional therapeutic agent may be in the same range as is typical for use of that agent as a monotherapy, or the concentration may be lower than a typical monotherapy concentration if there is synergy.

In other embodiments, a method according to the present invention utilizes a composition comprising an effective amount of a vegetable oil-derived polyol or hydrogel particles as the only active ingredient in the composition. In some embodiments, the hydrogel particles used in the method according to the present invention are not loaded or otherwise chemically associated with any additional therapeutic agent and/or imaging agent. In some embodiments, the hydrogel particles used in the method according to the present invention are not loaded with any cargo.

In some embodiments, the present invention provides a method of reducing the viability of a cancerous cell or tumorous cell comprising introducing into an environment in which the cell exists, an effective amount of a vegetable oil-derived polyol such as linseed oil-derived polyol or hydrogel particles according to the present invention. In further embodiments, the linseed oil-derived polyol and hydrogel particles in the method according to the present invention selectively reduces the viability of cancerous cells or tumorous cells over healthy cells. In specific embodiments, a vegetable oil-derived polyol such as a linseed oil-derived polyol and hydrogel particles in the method according to the present invention selectively induce apoptosis of cancerous cells or tumorous cells over healthy cells. In particular embodiments, the cancerous or tumorous cells are those causing a gynecologic cancer, including a cancer in the cervix, vagina, vulva, uterus, fallopian tube, and/or ovary.

In one embodiment, the subject invention provides a method for disrupting/inhibiting the proliferation of cancerous cells, comprising introducing into an environment in which the cells exist, an effective amount of a vegetable oil-derived polyol such as a linseed oil-derived polyol or hydrogel particles according to the present invention. In further embodiments, the vegetable oil-derived polyol and hydrogel particles in the method according to the present invention selectively disrupts/inhibits the proliferation of cancerous or tumorous cells over healthy cells.

In some embodiments, the present invention provides a method of selectively targeting and imaging various tumors and/or tumor associated macrophages (TAMs), comprising introducing into the environment of a tumor, an effective amount of a vegetable oil-derived polyol such as a linseed oil-derived polyol or hydrogel particles according to the present invention. The hydrogel particles may or may not be magnetic. Visualization of the tumor and/or TAMs is possible at wavelengths, 450 to 750 nm and 710 to 810 nm. In some embodiments, the vegetable oil-derived polyol according to the invention is a linseed oil-derived polyol. TAMs located in the tumor microenvironment play a significant role in cancerous or tumorous cell survival and progression, including the angiogenesis, metastasis, and multidrug resistance.

In specific embodiments, the hydrogel nanoparticles and/or microparticles are introduced to the environment of target cells at a concentration ranging, for example, from 0.1 µg/ml to 500 µg/ml, from 1 µg/ml to 450 µg/ml, from 1 µg/ml to 400 µg/ml, from 5 µg/ml to 400 µg/ml, from 10 µg/ml to 350 µg/ml, from 10 µg/ml to 300 µg/ml, from 25 µg/ml to 250 µg/ml, from 50 µg/ml to 200 µg/ml, from 50 µg/ml to 150 µg/ml, from 75 µg/ml to 200 µg/ml, or from 100 µg/ml to 200 µg/ml.

In certain embodiments, a vegetable-oil derived polyol such as a linseed oil-derived polyol by itself is introduced to the environment of target cells at a concentration ranging, for example, from about 0.001% to about 2.00%, from about 0.001% to about 1.00%, from about 0.001% to about 0.90%, from about 0.001% to about 0.80%, from about 0.001% to about 0.70%, from about 0.001% to about 0.60%, from about 0.001% to about 0.50%, from about 0.001% to about 0.40%, from about 0.001% to about 0.30%, from about 0.001% to about 0.20%, or from about 0.001% to about 0.10% by weight of the total composition. In some embodiments, a composition comprises a vegetable oil-derived polyol such as a linseed oil-derived polyol according to the present invention at from about 0.001% to about 0.09%, from about 0.001% to about 0.08%, from about 0.001% to about 0.07%, from about 0.001% to about 0.06%, from about 0.001% to about 0.05%, from about 0.001% to about 0.04%, from about 0.001% to about 0.03%, from about 0.001% to about 0.02%, from about 0.001% to about 0.01% by weight of the total composition.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

Unless specifically stated or obvious from context, as used herein, the term "or" is understood to be inclusive.

Unless specifically stated or obvious from context, as used herein, the terms "a," "and" and "the" are understood to be singular or plural.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., sub-ranges within the disclosed range), specific embodiments therein are intended to be explicitly included. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19 and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

EXAMPLES

Following are Examples which are offered by way of illustration and are not intended to limit the invention. Various modifications or changes in light thereof will be suggested to persons skilled in the art and are to be included within the spirit and purview of this application. Unless otherwise stated, these Examples utilized the methods, techniques, and materials as described in Materials and Methods above and known to those skilled in the art.

Materials and Methods:

Chitosan (448877-50G, Sigma-Aldrich), HEC (22-300 mPa·s, 2% in water at 20° C., TCI, 9004-62-0), Heavy liquid paraffin oil: Density: 0.8660-0.890 Kg/m$^3$, Tween 80, ethanol ("EtOH"), n-Hexane (Sigma-Aldrich), Glycine (Mwt. 75.07 g/mol: Density 1.607 g/cm3), linseed oil, glacial acetic acids, glutaraldehyde, hydrogen peroxide, diethyl ether, acetic anhydride (Sigma-Aldrich) were used as received. Linseed oil-derived polyol was prepared using standard protocols as described herein and in Sharmin et al., 2007. Millipore Sigma Deionized water from Millipore mille U10 water purification system was used in the preparation of hydrogels and other in vitro experiments.

The "vehicle" as used in the Examples refers to 100% EtOH. The linseed oil-derived polyol and nanogels were dissolved in EtOH in the percentages as described in the Examples.

Human Ovarian Microvascular Endothelial Cells (HOMEC) (Catalog No. #7300) were obtained from Sciencell. Endothelial Cell Medium (ECM, Catalog No. #1001) was used for culturing HOMEC in vitro experiments. ECM complete media was prepared using 500 ml of basal medium, 25 ml of fetal bovine serum (FBS, Catalog No. 0025), 5 ml of endothelial cell growth supplement (ECGS, Catalog No. 1052), and 5 ml of antibiotic solution (P/S, Catalog No. 0503). SKOV3 cells were obtained from ATCC HTB-77TH. ATCC-formulated McCoy's 5a Medium (modified) (Catalog No. 30-2007) was supplemented with 10% FBS. HeLa cell lines were obtained from ATCC.org (CCL-2™). Healthy human ovarian epithelial cells (HOSEpic) (Catalog No. #7310) were obtained from ScienCell. Ovarian Epithelial Cell Medium (OEpiCM, Catalog No. #7311) was used for culturing HOSEpiC in vitro.

Methods of Cytotoxicity Studies of Examples 2-4 (FIGS. 1, 6, and 7): Biocompatibility was assessed using the CyQUANT™ XTT Cell Viability Assay (Catalog No. X12223), obtained from Invitrogen. XTT (2,3-Bis-(2-Methoxy-4-Nitro-5-Sulfophenyl)-2H-Tetrazolium-5-Carboxanilide) and an electron coupling reagent was used to prepare the working solution according to the manufacturer's instructions. Human Ovarian Microvascular Endothelial Cells (HOMEC), healthy human ovarian epithelial cells (HOSEpic), SKOV3 cells, and/or HeLa cells (where applicable) were seeded in a 96-well plate (1×104 cells per well), and after 24 hours of incubation at 37° C., the medium was replaced with 100 µl of fresh medium containing 0.001-100 µg/ml nanogels or 100 µl of linseed oil-derived polyol (0.02%, 0.04%, 0.08%). Cells were treated with these various concentrations and incubated for 24 hours. 1 mg/ml of XTT and 2.5 µl of phenazine methosulfate (PMS) solution was freshly prepared and added (25 µl) to each well. The XTT-containing wells were incubated for 4 hours at 37° C. A multi-mode microplate reader (Synergy HT) was used to measure the absorbance at 450 nm wavelength. The experiments were performed in triplicates (n=3). Results are graphed as mean±standard deviation. The statistical analysis was done using Two-way analysis of variance (ANOVA) and by Tukey's multiple comparison test. Differences were considered significant if p<0.05.

Caspase-3/7 Assays of Examples 5-6 (FIGS. 2, 3, and 4): CellEvent™ Caspase-3/7 Green Flow Cytometry Assay Kit (Catalog No. C1042) from Invitrogen™ was used for detection of activated caspase-3 and caspase-7 in apoptotic cells treated with increasing concentrations of nanogels (0.1-100 µg/ml) or increasing concentrations of (0.004%, 0.008%, and 0.016%) of linseed oil-derived polyol in the vehicle. Human Ovarian Microvascular Endothelial Cells (HOMEC) and SKOV3 were exposed to the vehicle, increasing concentrations of nanogels (0.1-100 µg/ml), or increasing concentrations (0.004%, 0.008%, and 0.016%) of linseed oil-derived polyol for 48 hours. Caspase-3/7 assay was performed according to manufacturer's instructions.

Assay of angiogenesis factors of Example 7 (FIG. 5): Human Angiogenesis ELISA Strip I for Profiling 8 Cytokines (Catalog No. EA-1011) was used to study the effects of the vehicle and linseed oil-derived polyol on 8 human angiogenesis cytokines: TNF-α, IGF-1, VEGF, IL-6, FGFb, TGFb, EGF, Leptin. The ELISA was performed according to manufacturer's instructions. Briefly, standard curve was made using Protein Standards for Human Angiogenesis ELISA Strip (Catalog No. EA-1012). 100 µl of nanogels according to Example 1 and linseed oil-derived polyol supernatant was added to the ELISA strip and incubated for 2 hours at room temperature with gentle shaking. Furthermore, each well was washed by adding 200 µl of 1× assay wash buffer, and this step was repeated three times. After the last wash, the liquid was completely removed by inverting the plate against clean paper towels. Thereafter, 100 µl of diluted biotin-labeled antibody mixture was added to each well and incubated for 1 hour at room temperature with gentle shaking followed by the same washing steps. Streptavidin-HRP conjugate 100 µl was added to each well and incubated for 45 minutes with gentle shaking at room temperature. Further washing steps were repeated. Next was the addition of 100 µl of the substrate to each well, and incubation lasted for 30 mins. Lastly, 50 µl of stop solution was added to each well. As soon as the color of the wells changed from blue to yellow, the optical density of each well was determined using a microplate reader at 450 nm within 30 mins.

Methods of Molecular Docking Studies of Example 8 (FIGS. 8, 9A, and 9B): Molecular docking of linseed oil-derived polyol was performed with AutoDock Vina, version 1.1.2 and MGLTools, version 1.5.7 (see Eberhardt, J. et al., *AutoDock Vina 1.2.0: New Docking Methods, Expanded Force Field, and Python Bindings*, J. Chem. Information and Modeling, 61(8), 3891-898 (2021); Trott, O. et al., *AutoDock Vina: Improving the Speed and Accuracy of Docking with a New Scoring Function, Efficient Optimization, and Multithreading*. J. Comp. Chem., 31(2), 455-461 (2010); Morris, G. et al. *Autodock4 and AutoDockTools4: Automated Docking with Selective Receptor Flexibility*, J. Comp. Chem. 30(16): 2785-91 (2009)). Figures of the complexes were created with UCFS ChimeraX 1.3 (see, e.g., Pettersen, E. et al., *UCSF Chimera—a Visualization System for Exploratory Research and Analysis*, J Comput. Chem., 25(13), 1605-12 (2004)).

Example 1—Preparation of Hydrogel Nanoparticles (Nanogels) According to the Present Invention This Example provides a representative process of preparing hydrogel nanoparticles (nanogels) that were used in Examples 3, 4, and 6.

Nanogels of chitosan (0.7 g) and HEC (0.3 g) with linseed oil-derived polyol as a hydrophobic modifier (1 ml of 2%) according to the present invention were prepared in a beaker using a water-in-oil emulsion polymerization method.

A polymer solution (40 ml) of 2% (w/v) polymers (chitosan and HEC) was prepared in 1% (v/v) acetic acid. A separate beaker was used to make a mixture of liquid paraffin oil and 1% (w/w) Tween 80. The polymer solution was added dropwise to this mixture of oil and emulsifying agent stirred at 1400 rpm on a magnetic stirrer. The mixing of the combined solution was continued for 20 minutes, followed by the addition of glutaraldehyde (5 ml) and stirring for another 10 minutes. The linseed oil-derived polyol was added to the reaction mixture and stirring was continued at 1400 rpm for 6 hours. The particles were washed thoroughly with n-hexane to remove excess oil. Any excess glutaraldehyde was deactivated by 0.1 M glycine. The washed hydrogel particles were dried at room temperature.

Example 2—Linseed Oil-Derived Polyol Selectively Reduces the Viability of SKOV3

Healthy human ovarian epithelial cells (HOSepic) and human ovarian cancer cells (SKOV3) were exposed to the vehicle or increasing concentrations (0.02%, 0.04%, and 0.08%) of linseed oil-derived polyol for 48 hours. The XTT cell viability assay was performed according to the manufacturer's instructions and the method described above. As shown in FIG. 1, linseed oil-derived polyol negatively affects the viability of cancerous cells (SKOV3) while promoting the proliferation in healthy cells (HOSepic).

Example 3—Nanogels Selectively Reduce the Viability of SKOV3 and HeLa

Figure 6:
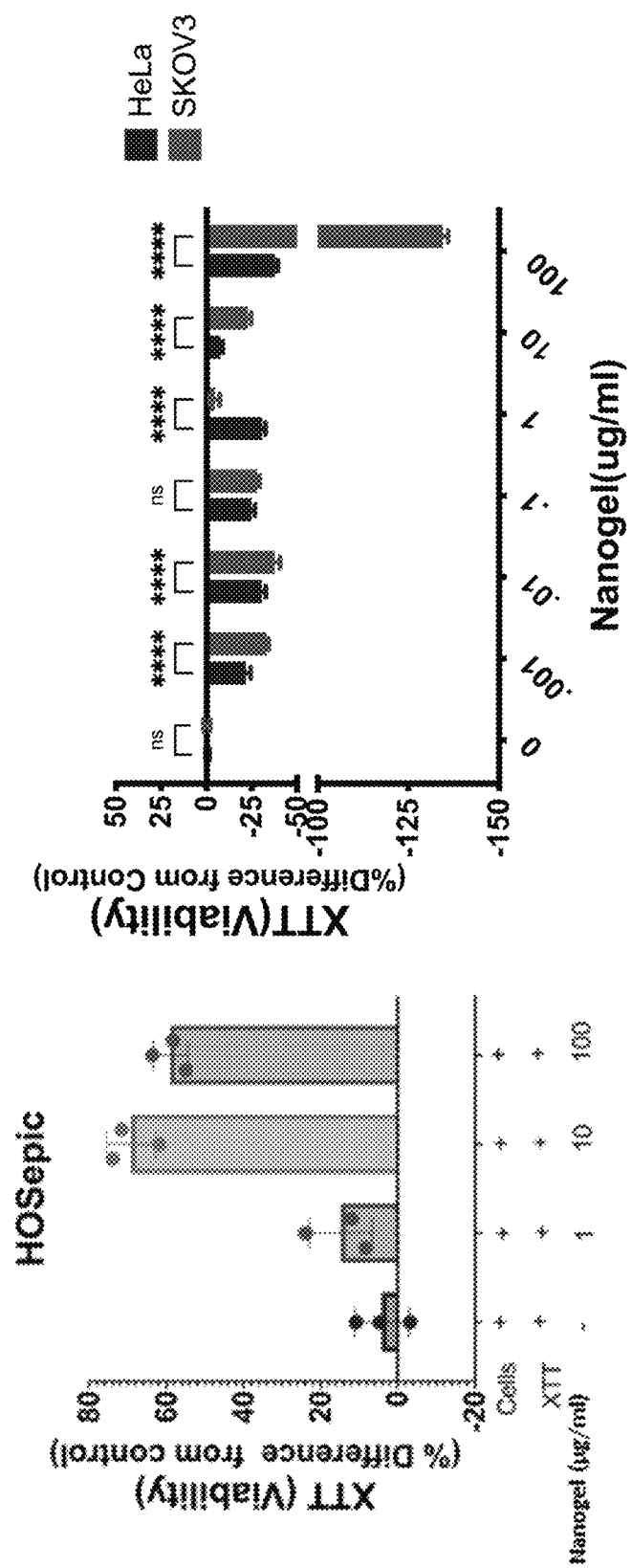
FIG. 6 provides graphs showing differences in viability of healthy human ovarian epithelial cells (HOSepic), human ovarian cancer cells (SKOV3), and HeLa cells after exposure to increasing concentrations of nanogels comprising linseed oil-derived polyol.

Healthy human ovarian epithelial cells (HOSepic), human ovarian cancer cells (SKOV3), and human cervical cancer cells (HeLa) were exposed to the vehicle or increasing concentrations (e.g., 1 µg/ml, 10 µg/ml, 100 µg/ml) of nanogels according to the present invention for 48 hours. The XTT cell viability assay was performed according to the manufacturer's instructions and the method described above. As shown in FIG. 6, SKOV3 and HeLa are sensitive to nanogel-induced toxicity than HOSEpic.

Example 4—Nanogels Selectively Reduce the Viability of SKOV3

Figure 7:
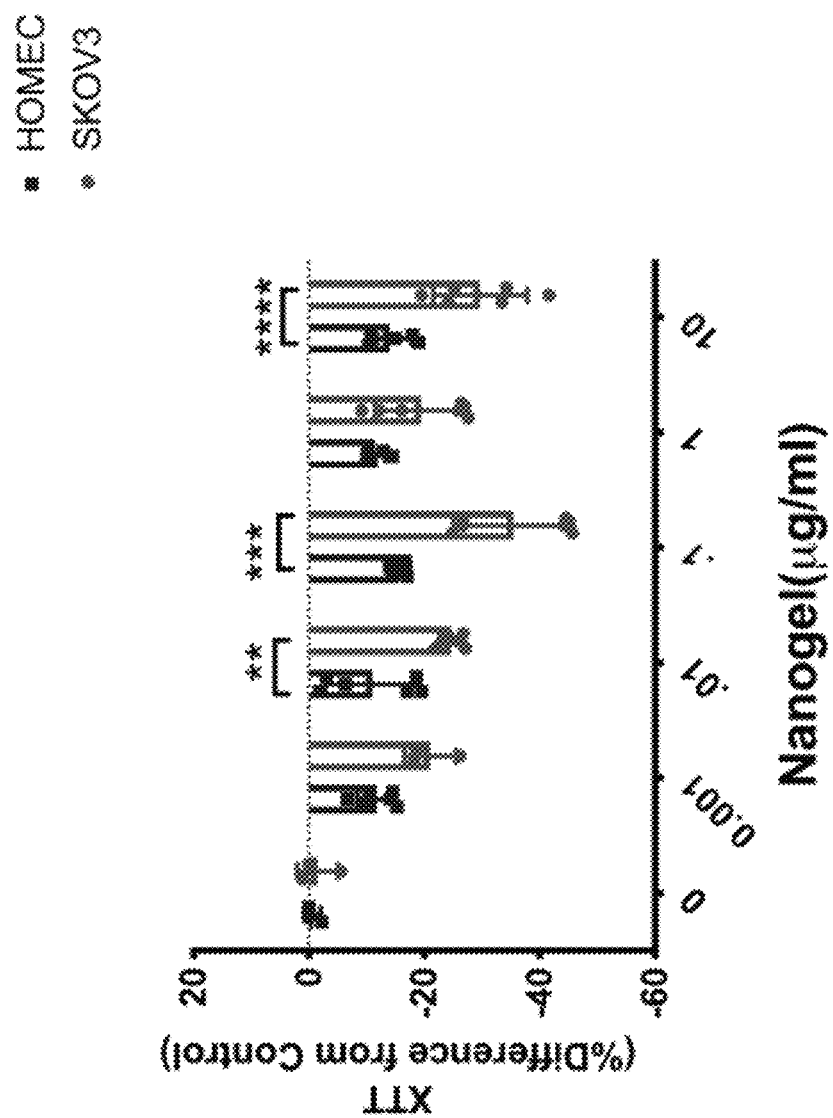
FIG. 7 provides a graph showing the results of the XTT cell viability assay of healthy human ovarian epithelial cells (HOMEC) and human ovarian cancer cells (SKOV3) after exposure to increasing concentrations (0-10 µg/ml) of nanogels comprising linseed oil-derived polyol.

Healthy human ovarian endothelial cells (HOMEC) and human ovarian cancer cells (SKOV3) were exposed to the vehicle or increasing concentrations of nanogels according to the present invention for 48 hours. The XTT cell viability assay was performed according to the manufacturer's instructions and the method described above. As shown in FIG. 7, SKOV3 are more sensitive to nanogel-induced toxicity than HOMEC. Nanogels (NG) induce apoptosis of cancerous (SKOV3) cells but has significantly less impact on healthy cells (HOMEC). Statistical significance two-way ANOVA, Tukey's post hoc analysis, $p<0.01$, *$p$-value $<0.001$, and ***$p$-value $<0.0001$.

Example 5—Linseed Oil-Derived Polyol Selectively Induces Apoptosis in SKOV3

Figure 2:
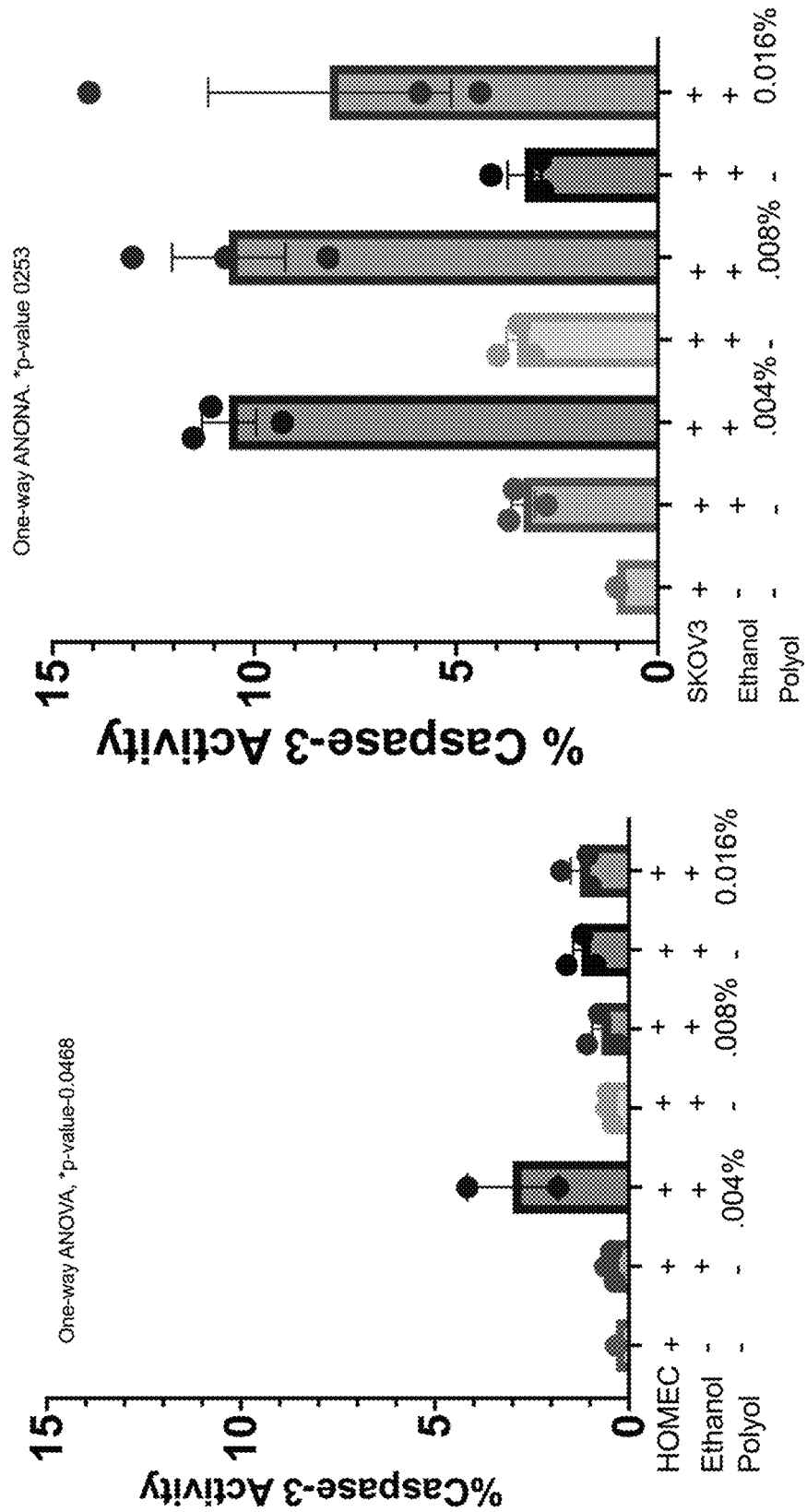
FIG. 2 provides graphs showing the results of the Caspase-3 Activity Assay showing the degree of apoptosis in healthy human ovarian epithelial cells (HOMEC) and human ovarian cancer cells (SKOV3) after exposure to increasing concentrations of linseed oil-derived polyol.
Figure 3:
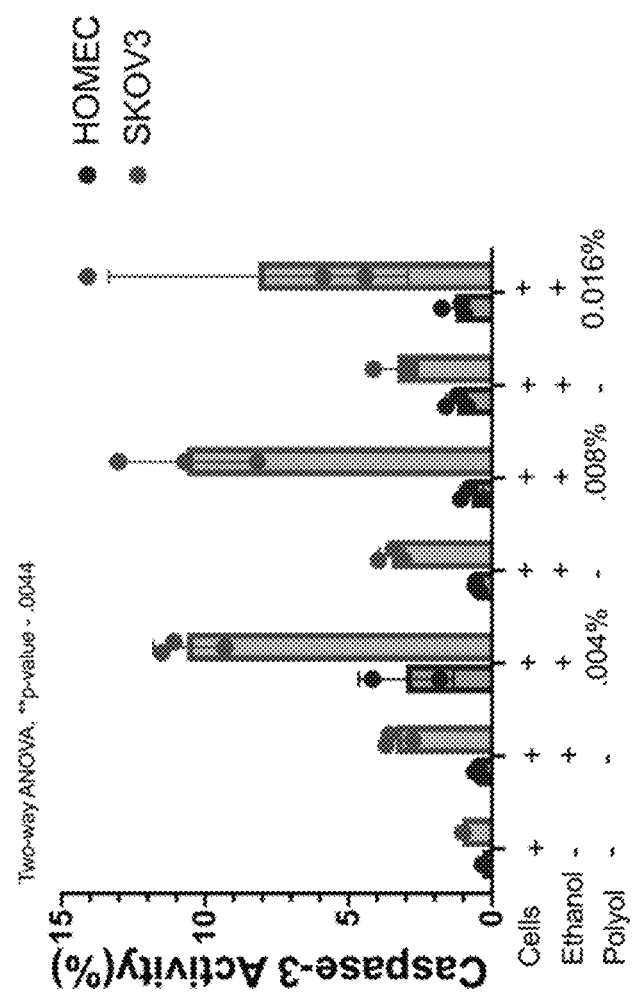
FIG. 3 provides a comparative analysis of Caspase-3 activity (%) in healthy human ovarian epithelial cells (HOMEC) and human ovarian cancer cells (SKOV3) after exposure to increasing concentrations of linseed oil-derived polyol.

Human Ovarian Microvascular Endothelial Cells (HOMEC) and human ovarian cancer cells (SKOV3) were exposed to the vehicle or increasing concentrations (0.004%, 0.008%, and 0.016%) of linseed oil-derived polyol for 48 hours. Caspase-3/7 assay was performed according to manufacturer's instructions and the method described above. As shown in FIGS. 2 and 3, linseed oil-derived polyol induces apoptosis of cancerous cells (SKOV3) significantly more than healthy cells (HOMEC).

Example 6—Nanogels Selectively Induce Apoptosis in SKOV3

Figure 4:
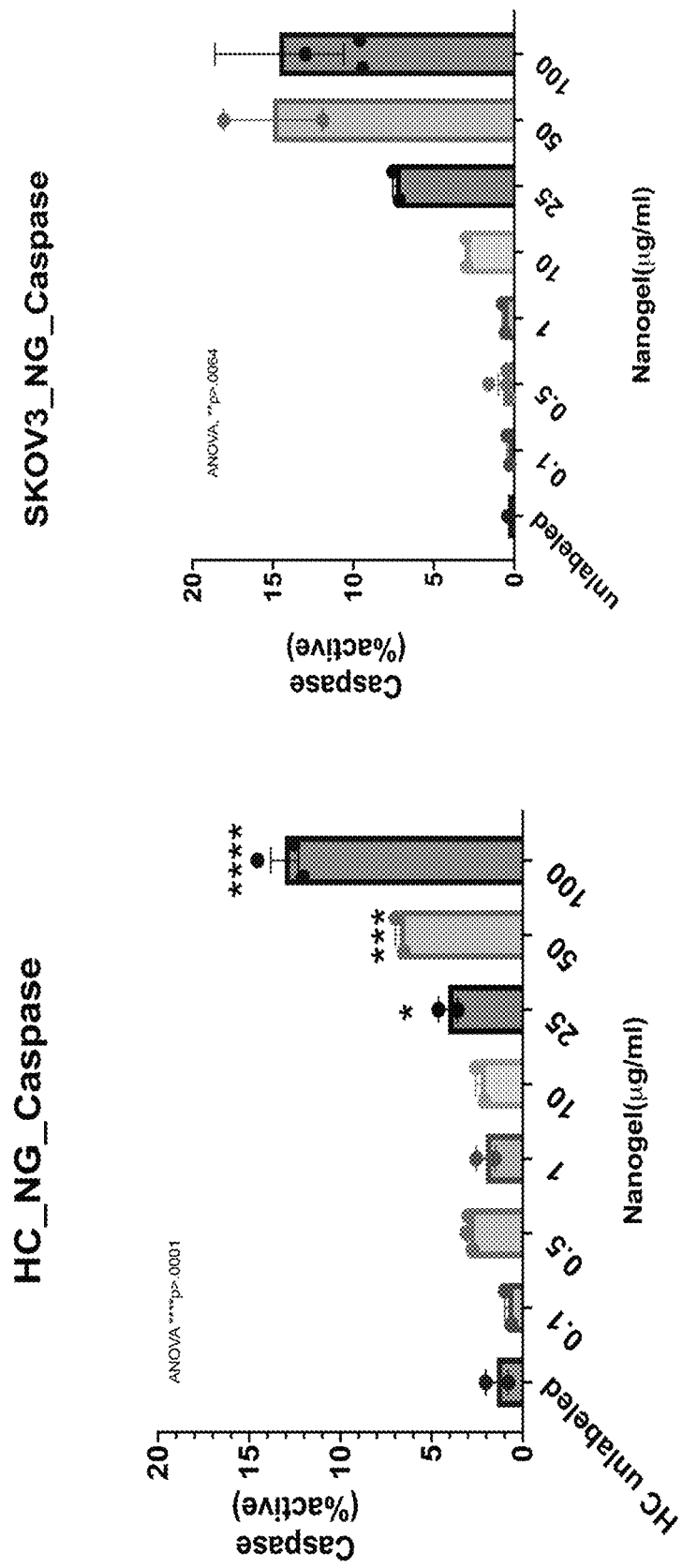
FIG. 4 provides graphs showing the results of the Caspase-3 Activity Assay showing the degree of apoptosis in healthy human ovarian epithelial cells (HOMEC) and human ovarian cancer cells (SKOV3) after exposure to increasing concentrations of nanogels comprising linseed oil-derived polyol.

Human Ovarian Microvascular Endothelial Cells (HOMEC) and human ovarian cancer cells (SKOV3) were exposed to the vehicle or increasing concentrations (0.1 µg/ml, 0.5 µg/ml, 1 µg/ml, 10 µg/ml, 25 µg/ml, 50 µg/ml, 100 µm/ml) of nanogels according to the present invention for 48 hours. Caspase-3/7 assay was performed according to manufacturer's instructions and the method described above. As shown in FIG. 4, at higher doses of nanogels, SKOV3 cells are more sensitive to nanogel-induced apoptosis than apoptosis induced by linseed oil-derived polyol in cancerous (SKOV3) cells or healthy cells (HOMEC).

Example 7—Angiogenic Factors are Differentially Up-Regulated in SKOV3 by Linseed Oil-Derived Polyol A study was conducted to observe the effects of the vehicle and linseed oil-derived polyol (0.02%) on 8 human angiogenesis cytokines: TNF-α, IGF-1, VEGF, IL-6, FGFb, TGFb, EGF, Leptin.

Figure 5:
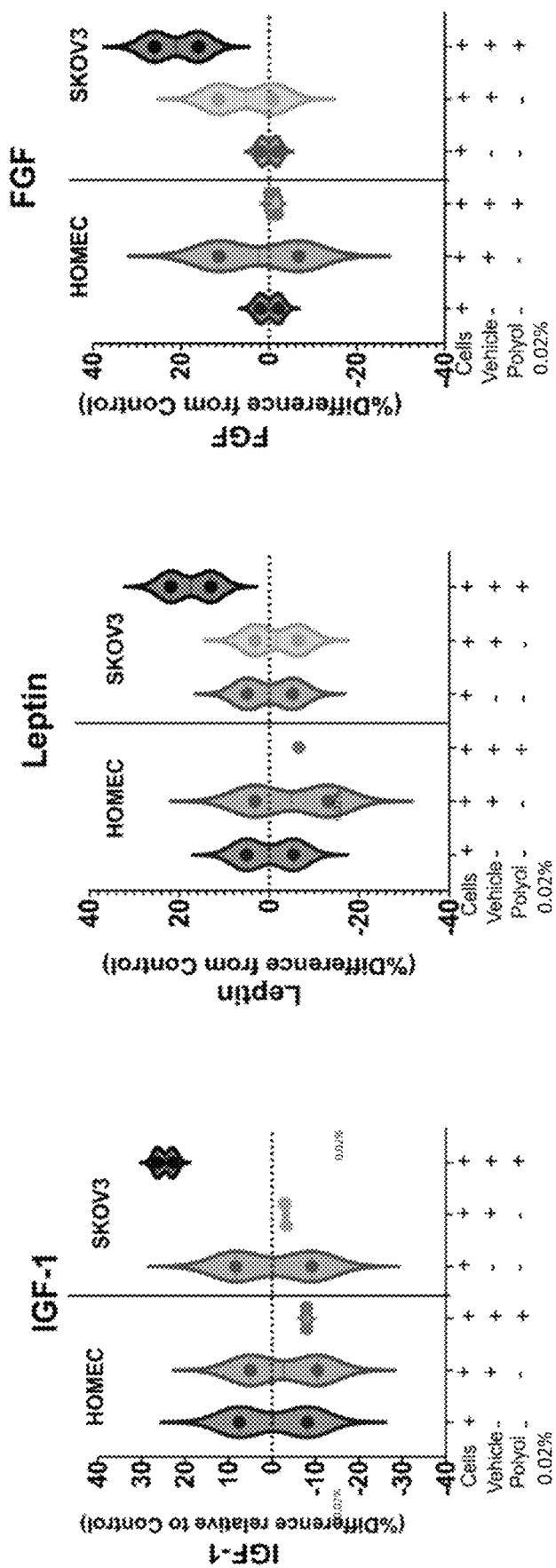
FIG. 5 provides graphs showing angiogenic factors being differentially up-regulated in human ovarian cancer cells (SKOV3) by linseed oil-derived polyol.

As shown in FIG. 5, the three angiogenic factors IGF-1, Leptin, FGFb were upregulated in SKOV3 but not in HOMEC when exposed to linseed oil-derived polyol (0.02%).

Example 8—Molecular Docking Studies Show Interactions of Linseed Oil-Derived Polyol with Leptin, Leptin Receptor, and IGF-1R Molecular docking studies are used to predict the binding affinities of various ligands. Here, docking studies were conducted to assess the interactions of linseed oil-derived polyol with leptin, leptin receptor, and IGF-1 receptor (IGF-1R).

Leptin promotes vascularization, proliferation, migration and invasion of tumor cells. Leptin is intricately involved in signaling as well as interactions with other hormones in connection with cancer development and progression, including gynecologic cancers. Thus, leptin is an attractive pharmaceutical target for cancer treatment.

Figure 8:
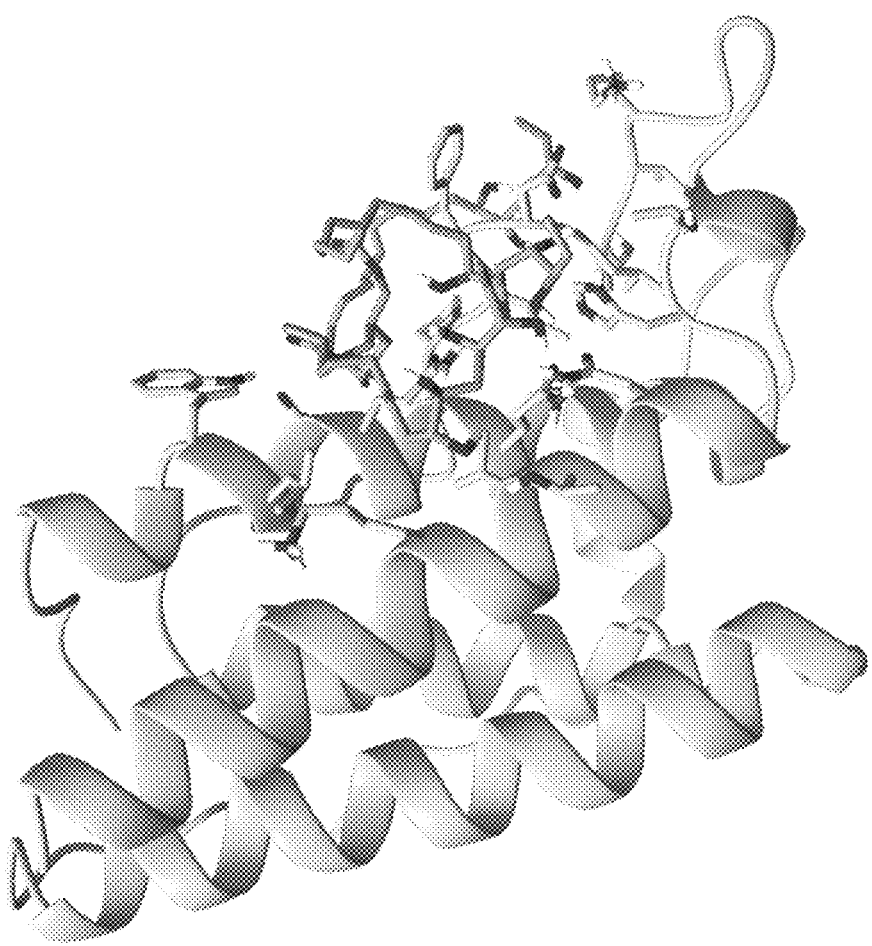
FIG. 8 provides an image from a docking study of the linseed oil-derived polyol binding to Leptin (PDB ID 1AX8).

The inventors have hypothesized that leptin (PDB ID 1AX8) has several surface-exposed hydrophobic residues, allowing interactions with linseed oil-derived polyol. As shown in FIG. 8, the backbone of linseed oil-derived polyol makes non-specific interactions with these hydrophobic residues, while at the same time makes hydrogen-bond interactions with polar and charged residues of leptin. Moreover, linseed oil-derived polyol may interact with leptin receptor (pdb ID 3V6O) as shown in FIG. 9B, blocking the interaction of leptin with this receptor.

Figure 9A:
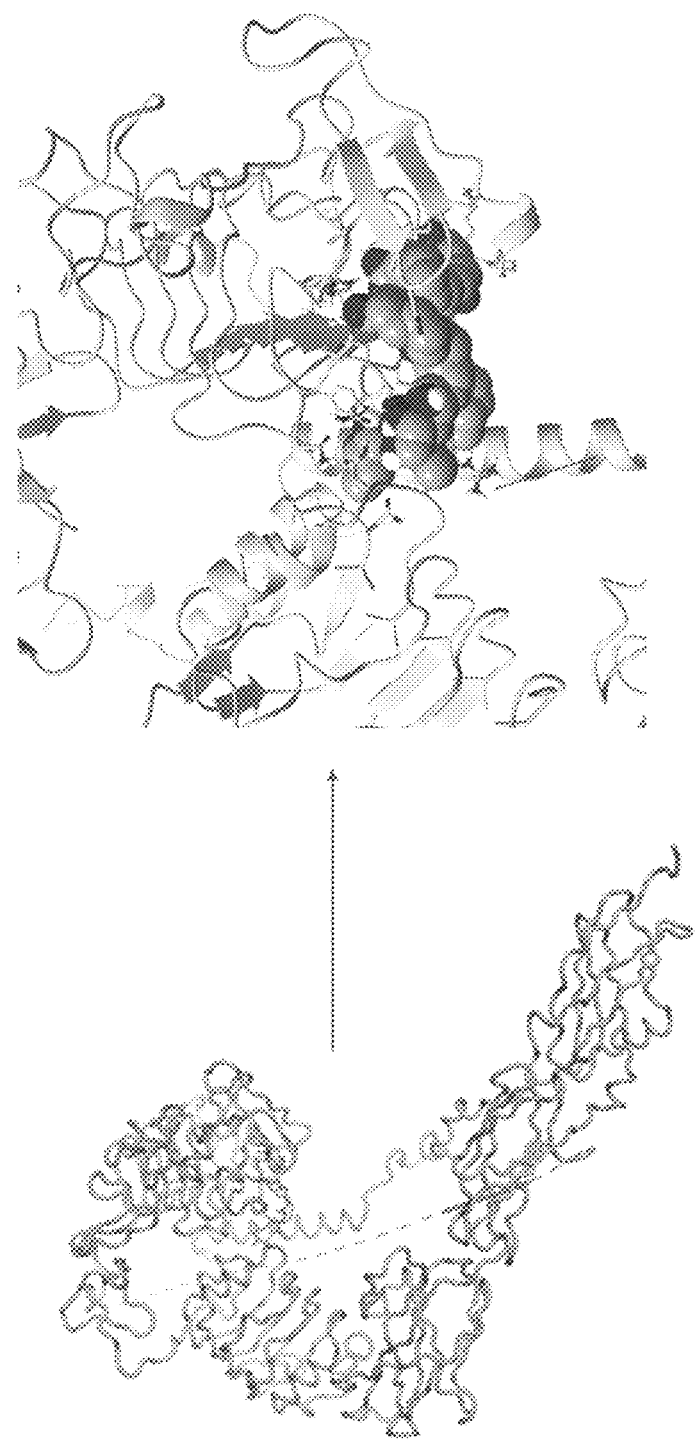
FIG. 9A provides an image from a docking study of the linseed oil-derived polyol binding to IGF-1R insulin (PDB ID 6JK8).
Figure 9B:
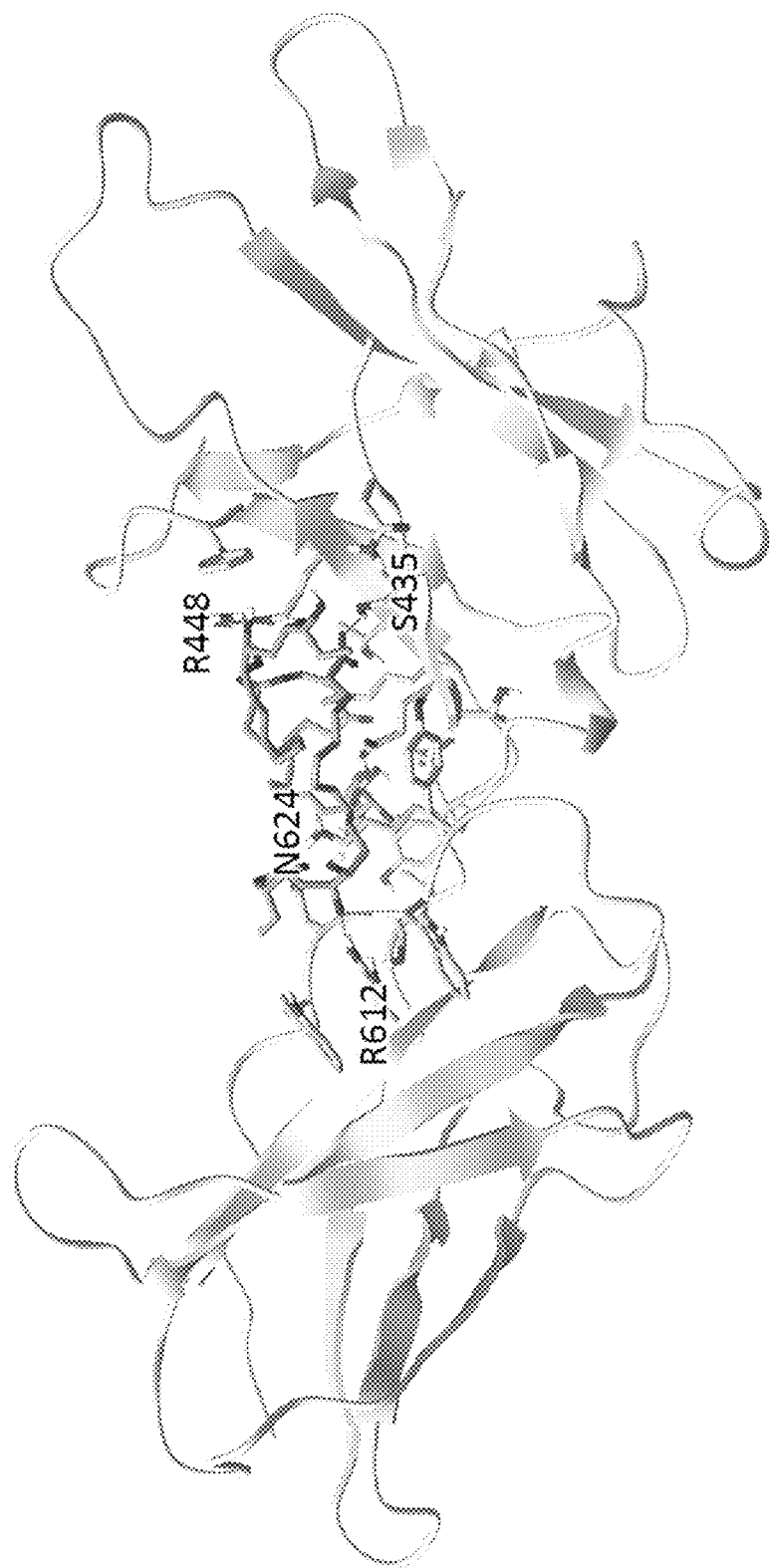
FIG. 9B provides an image from a docking study of the linseed oil-derived polyol binding to Leptin receptor (PDB ID 3V6O).

Similarly, linseed oil-derived polyol may also interact with the insulin-like growth factor type 1 receptor (IGF-1R) as shown in FIG. 9A. The predicted binding site is near the IGF-1 binding site, suggesting the polyol's ability to block the interaction of IGF-1 and its receptor. As IGF-1 signaling system plays a key role in the maintenance and development of cancer including ovarian cancer, IGF-1R is also an attractive target for cancer treatment.

What is claimed is:

1. A pharmaceutical composition for treating a cancer or tumor in a subject, comprising an effective amount of vegetable oil-derived polyol as an active ingredient and a carrier and/or excipient, said vegetable oil-derived polyol comprising a compound of the formula (I):

2. The composition according to claim 1, said cancer or tumor being a gynecologic cancer or tumor.

3. The composition according to claim 1, said cancer or tumor being an ovarian, cervical, and/or a fallopian tube cancer or tumor.

4. The composition according to claim 1, said cancer being an ovarian cancer.

5. The composition according to claim 1, said linseed oil-derived polyol being a component of biopolymer-based hydrogel nanoparticles and/or microparticles, said biopolymer-based hydrogel nanoparticles and/or microparticles comprising a gel of one or more biopolymer, and no magnetic material or cargo.

6. A method of treating ovarian cancer and/or cervical cancer tumor in a subject, comprising administering to the subject in need of such treatment the pharmaceutical composition of claim 1.

7. The method according to claim 1, said vegetable oil-derived polyol being a component of hydrogel nanoparticles and/or microparticles.

8. The method according to claim 7, said hydrogel nanoparticles and/or microparticles comprising a gel of chitosan and hydroxyethyl cellulose (HEC).

9. The method according to claim 8, said hydrogel nanoparticles and/or microparticles serving as an imaging agent without carrying an additional therapeutic or imaging agent.

10. The method according to claim 7, said hydrogel nanoparticles and/or microparticles not comprising a magnetic component.

11. The method according to claim 7, said hydrogel nanoparticles and/or microparticles not carrying a cargo.

12. The method according to claim 1, said vegetable oil-derived polyol and not forming a component of hydrogel nanoparticles and/or microparticles.

13. A method of selectively imaging a tumor and/or tumor associated macrophages (TAMs), comprising introducing into the environment of said tumor, an effective amount of hydrogel nanoparticles and/or microparticles comprising a gel of one or more biopolymer and a vegetable oil-derived polyol; the vegetable oil-derived polyol comprising a compound of the formula (I):

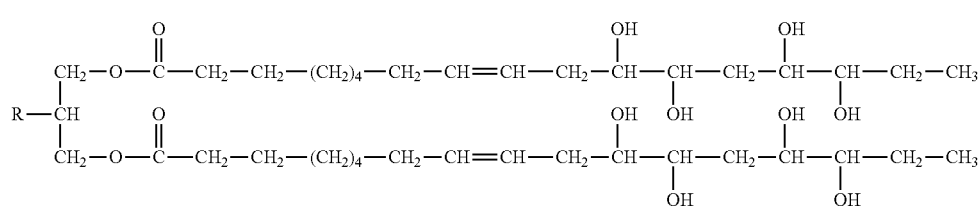

R being:

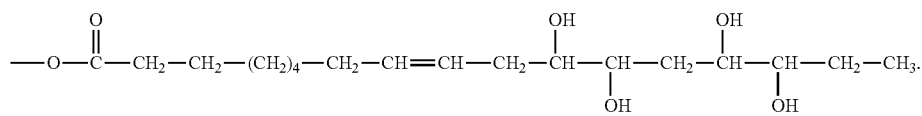

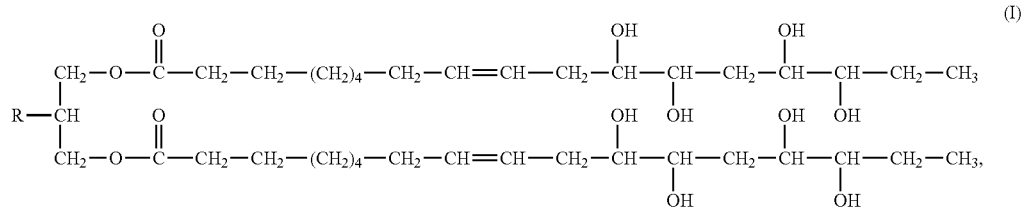

(I)

R being

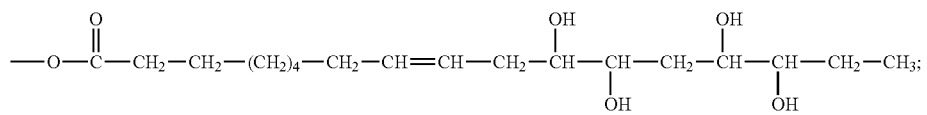

and
visualizing said tumor and/or TAMs at wavelengths 450 to 750 nm and 710 to 810 nm.

14. A pharmaceutical composition consisting of an effective amount of vegetable oil-derived polyol as an active ingredient and a carrier and/or excipient said vegetable oil-derived polyol comprising a compound of the formula (I):

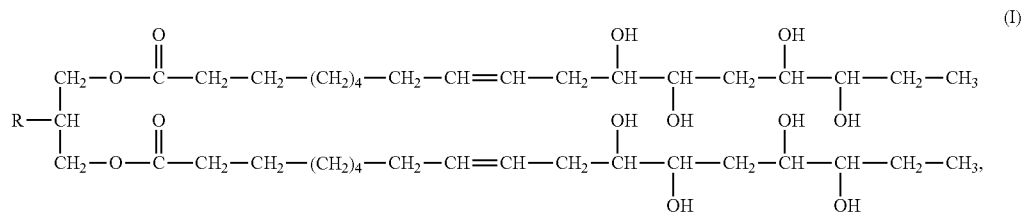

(I)

R being

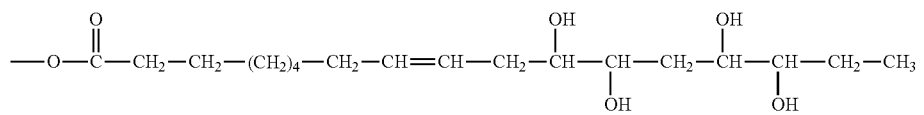

15. A method of treating ovarian cancer and/or cervical cancer in a subject, comprising administering to the subject in need of such treatment the pharmaceutical composition of claim 14.

* * * * *